(12) United States Patent
Thompson et al.

(10) Patent No.: US 7,374,944 B2
(45) Date of Patent: May 20, 2008

(54) DEVICE AND BIOANALYTICAL METHOD UTILIZING ASYMMETRIC BIOFUNCTIONALIZED MEMBRANE

(75) Inventors: David H. Thompson, West Lafayette, IN (US); Christine A. Hrycyna, Lafayette, IN (US); Gil U. Lee, West Lafayette, IN (US); Osman A. Basaran, West Lafayette, IN (US); Kinam Park, West Lafayette, IN (US); Igal Szleifer, Homewood, IL (US)

(73) Assignee: Purdue Research Foundation, West Lafayette, IN (US)

( * ) Notice: Subject to any disclaimer, the term of this patent is extended or adjusted under 35 U.S.C. 154(b) by 539 days.

(21) Appl. No.: 10/491,686

(22) PCT Filed: Oct. 3, 2002

(86) PCT No.: PCT/US02/31772

§ 371 (c)(1),
(2), (4) Date: Jul. 23, 2004

(87) PCT Pub. No.: WO03/052420

PCT Pub. Date: Jun. 26, 2003

(65) Prior Publication Data

US 2005/0175501 A1    Aug. 11, 2005

Related U.S. Application Data

(60) Provisional application No. 60/326,862, filed on Oct. 3, 2001.

(51) Int. Cl.
*G01N 33/00* (2006.01)

(52) U.S. Cl. .......................... 436/86; 436/71; 436/169; 422/56; 422/58

(58) Field of Classification Search ................. 436/71, 436/86, 169; 422/56, 58, 61; 435/287.1, 435/287.7
See application file for complete search history.

(56) References Cited

U.S. PATENT DOCUMENTS

| 5,111,221 A | 5/1992 | Fare et al. | |
|---|---|---|---|
| 5,401,378 A | * 3/1995 | King et al. | ................. 205/778 |

(Continued)

FOREIGN PATENT DOCUMENTS

WO    WO 96/38726    12/1996

(Continued)

OTHER PUBLICATIONS

Christoph Bieri et al., "Micropatterned immobilization of a G protein-coupled receptor and direct detection of G protein activation", *Nature Biotechnology*, Nov. 1999, pp. 1105-1108, vol. 17, published by Nature America Inc., New York, NY USA.

(Continued)

*Primary Examiner*—Maureen M. Wallenhorst
(74) *Attorney, Agent, or Firm*—Woodard, Emhardt, Moriarty, McNett & Henry LLP

(57) ABSTRACT

Bioanalytical device that includes a biofunctional component and an optional sensor component. The device includes arrays of addressable, durable, asymmetric biofunctional membranes containing protein transducers capable of unidirectional transport of analytes. Suitable protein transducers include members of the ATP-binding cassette family, such as P-glycoprotein.

21 Claims, 12 Drawing Sheets

U.S. PATENT DOCUMENTS

| | | |
|---|---|---|
| 5,879,878 A | 3/1999 | Raguse et al. |
| 6,228,326 B1 | 5/2001 | Boxer et al. |

FOREIGN PATENT DOCUMENTS

| | | |
|---|---|---|
| WO | WO 97/01092 | 1/1997 |
| WO | WO 99/20649 | 4/1999 |
| WO | WO 01/70419 | 9/2001 |
| WO | WO 92/072873 | 9/2002 |

OTHER PUBLICATIONS

B. A. Cornell et al., "A biosensor that uses ion-channel switches", *Nature*, Jun. 5, 1997, pp. 580-583, vol. 387, published by Macmillan Magazines Ltd., London, England.

Jay T. Groves et al., "Electrical Manipulation of Glycan-Phosphatidyl Inositol-Tethered Proteins in Planar Supported Bilayers", *Biophysical Journal*, Nov. 1996, pp. 2716-2723, vol. 17.

Joshua Salafsky et al., "Architecture and Function of Membrane Proteins in Planar Supported Bilayers: A Study with Photosynthetic Reaction Centers", *American Chemical Society*, 1996, pp. 14773-14781, vol. 35.

Burkhard Raguse et al., "Tethered Lipid Bilayer Membranes: Formation and Ionic Reservoir Characterization", *Langmuir The ACS Journal of Surfaces and Colloids*, Feb. 3, 1998, pp. 648-659, vol. 14 No. 3, published by the Amereican Chemical Society, Washington, DC, USA.

Jay T. Groves et al., "Control of Cell Adhesion and Growth with Micropatterned Supported Lipid Membranes", *Langmuir The ACS Journal of Surfaces and Colloids*, Aug. 21, 2001, pp. 5129-5133, vol. 17 No. 17, published by the American Chemical Society, Washington, DC, USA.

Sackmann E E et al., "Supported membranes on soft polymer cushions: fabrication, characterization and applications", *Trends in Biotechnology*, Feb. 2000, pp. 58-64, vol. 18, Elsevier, Amsterdam, NL.

Hendrik W. Van Veen et al., "The ABC family of multidrug transporters in microorganisms", *Biochimica et Biophysica Acta*, 1998, pp. 31-36.

J Yuto et al., Database "ATP-sensitive anion channel from rat brain synaptosomal membranes incorporated into planar lipid bilayers", Database Biosis Online Biosciences Information Service, *Biophysical Journal*, pp. 720-727, 1997, Philadelphia, PA.

http://nutrigene.4t.com/humanabc.htm, "48 Human ATP-Binding Cassette Transporters".

Christine Hrycyna, slide presentation: "Highthroughput Assay Technology for Membrane Proteins", summer 2002.

David H. Thompson, slide presentation: "Naturally Occurring Bolaamphiphile (Archaeol)", presented Mar. 28, 2002.

* cited by examiner

A

B

Cyclic Voltammetry

SSC20BAS-DPPC

A

DPPC

SSC20BAS-C20BAS-GA

B

C20BAS-GA

DEVICE AND BIOANALYTICAL METHOD UTILIZING ASYMMETRIC BIOFUNCTIONALIZED MEMBRANE

This application claims the benefit of U.S. Provisional Application Ser. No. 60/326,862, filed 3 Oct. 2001, which is incorporated herein by reference in its entirety.

BACKGROUND OF THE INVENTION

The design and synthesis of bioinspired materials such as synthetic light harvesting complexes, artificial ion channels, artificial muscles, has captured the imagination of many individual research groups. Very few efforts, however, have been directed toward the full integration of biologic and synthetic materials for the creation of hybrid biofunctional devices. Accomplishments in the area of bacteriorhodopsin-based optoelectronic devices (Birge, *IEEE Comput.* 25, 56 (1992)), gramicidin-based biosensors (Cornell et al., *Nature* 387, 580-583 (1997)), and photochemical triad-driven ATP synthase processes (Steinberg-Yfrach et al., *Nature* 392, 479-482 (1998)) constitute important advances that have involved multidisciplinary investigative groups to direct the design, synthesis, processing, structural analysis, and performance testing of these devices.

It has been 20 years since the first demonstration that Langmuir-Blodgett films could be used to assemble lipid bilayers on solid surfaces (Von Tschamer et al., *Biophys. J.* 36(2), 421-427 (1981)). This initial work inspired intense interest in biotechnologies based on supported lipid bilayers because of the important role that membrane proteins play in living systems. Unfortunately, applications of supported lipid membranes have been limited by their instability. Recent breakthroughs by Cornell et al (Nature, 1997, 387: 580) and Bieri et al. (Nature Biotechnol., 1999, 17:1105) in anchoring chemistries and protein orientation, respectively, have produced durable asymmetric biofunctional membranes Channel proteins are embedded in the membranes to provide biofunctionality. Cornell et al. describe the incorporation of gramicidin dimers in membranes formed from a tethered lipid bilayer. Bieri et al. describe the use of conventional bilayers with the G-protein coupled receptor, bacteriorhodopsin. This protein is oriented with respect to the surface using a streptavidin-biotin interaction. Others have used a silyl-modified polyethylene glycol (PEG) to tether a supported membrane to glass.

Despite these advances, the stability of planar membrane structures remains an issue. Moreover, conventional methods are limited to the use of channel proteins and require chemical modification of the protein that is often non-specific or difficult to control. Biofunctional membranes exhibiting increased stability and/or broader utility are needed in order to meet the complex needs of nanotechnology and biotechnology.

SUMMARY OF THE INVENTION

Arrays of addressable, durable, asymmetric biofunctional membranes according to the present invention are capable of unidirectional transport of analytes such as chemical and biological agents, thereby enabling a number of new technologies including functional screening technologies of membrane proteins and their interaction with compounds of interest; chemical and biological agent detection and decontamination; bioprocess separations; and environmentally-responsive matrices (e.g., surgically-implanted drug reservoirs, dermal patches and subcutaneous implants) for drug delivery under feedback control. The active transport structures in these biofunctional devices are oriented in large arrays and supported to provide transport directionality and mechanical stability.

Accordingly, one aspect of the invention is directed to a bioanalytical device that includes a biofunctional component and, optionally, a sensor component. The biofunctional component includes, as components, a membrane film, a protein transducer directionally oriented within the membrane film, and a support substrate. The membrane film has an outer surface and an inner surface, such that the inner surface is in contact with an aqueous compartment that is disposed between the membrane film and the support substrate. The inner surface of the membrane is thus in fluid communication with the support substrate. The aqueous compartment preferably contains a detection moiety for detecting the activity of the protein transducer. Preferably, the activity of the protein transducer is detectable by detecting ATP hydrolysis.

Optionally, the biofunctional component of the bioanalytical device also includes a transducer orienting layer disposed between the membrane film and the support substrate. The transducer orienting layer may include one or more orienting moieties that interacts with the protein transducer to orient the protein within the membrane film. Alternatively or in addition, orienting moieties may be included on or within the support substrate. The transducer orienting layer may also include a detection moiety for detecting the activity of the protein transducer.

The membrane film can be formed from synthetic or naturally occurring components. It can take the form of a bilayer or a monolayer. Exemplary components of the membrane film include one or more lipids, bolalipids, bolaamphiphiles, triblock copolymers and/or a hydrogels.

The protein transducer can be, for example, a multi-drug resistance protein, a multi-drug resistance-associated proteins or mitoxantrone-resistance protein. A preferred protein transducer is a protein which is a member of the ATP-binding cassette superfamily, such as P-glycoprotein. Gramicidin is another preferred protein, and is especially useful in an embodiment of the device wherein the membrane film is a monolayer, such as that formed by a bolalipid or bolaamphiphile. In a monolayer film, the gramicidin can advantageously function as a monomer.

The support substrate can be formed from, for example, a nanoporous material or a solid. Examples of suitable materials include silicon, gold and γ-alumina. The device optionally includes a gold electrode having an orienting moiety attached thereto, such that the orienting molecule interacts with the protein transducer to orient the protein within the membrane film.

The optional sensor component of the bioanalytical device detects a signal generated upon operation of the biofunctional component. The signal is indicative of the activity of the protein transducer. This signal can be, for example, a chemical signal, an optical signal, an electrochemical signal, an electrical signal, and/or an electromagnetic signal.

The bioanalytical device is typically organized as an array of biofunctionalized membranes in fluid communication with the support substrate, the biofunctionalized membranes comprising the membrane film and the protein transducer directionally oriented with the membrane film. Advantageously, the biofunctional component of the bioanalytical device can be fabricated as a replaceable cartridge.

In another aspect, the invention includes a method for making the bioanalytical device. A biofunctional component can be fabricated by applying a hydrogel precursor solution to the surface of a support substrate; applying a gellating agent to the hydrogel precursor to cause gellation of the hydrogel precursors to yield a transducer orienting layer in physical contact with the surface of the support substrate; and applying a protein transducer and a membrane film material to the transducer orienting layer to yield a membrane film in fluid communication with the transducer orienting layer. The inner surface of the membrane film defines an aqueous compartment between the transducer orienting layer and the membrane film. Optionally, the transducer orienting layer is integrated into the support substrate.

In another aspect, the invention includes a method for analyzing an analyte, such as a drug, using a bioanalytical device as described herein. In one embodiment, the analyte is contacted with the outer surface of the membrane film of a bioanalytical device as described herein, such that the analyte passes into or across the membrane film. The activity of the protein transducer is then detected, wherein activity of the protein transducer is indicative of the efflux of the analyte from the outer surface of the membrane film. In an alternative embodiment, protein transducers having uptake activity rather then efflux activity can be used to analyze an analyte. Uptake of the analyte into the aqueous compartment is then detected.

In yet another aspect, the invention includes a method for identifying an inhibitor of a protein transducer using a bioanalytical device as described herein. In one embodiment, the outer surface of a membrane film is contacted with (a) an analyte capable of being actively transported by the membrane-embedded protein transducer and (b) a candidate inhibitor of the protein transducer. It is then determined whether the active transport of the analyte by the membrane-embedded protein transducer is inhibited by the candidate inhibitor compared to the active transport of the analyte by the membrane-embedded protein transducer in the absence of the candidate inhibitor. In another embodiment, the method can be used to identify an inhibitor of a protein transducer having uptake activity instead of efflux activity.

In yet another aspect, the invention includes a kit for making a bioanalytical device which includes, as components, membrane film material; hydrogel precursors; support substrate; and packaging and instructions for use of the bioanalytical device for analysis of the activity of a membrane-embedded protein transducer.

DETAILED DESCRIPTION OF ILLUSTRATIVE EMBODIMENTS

The present invention provides a platform for the creation of arrays of addressable, durable asymmetric biofunctional membranes that are capable of unidirectional transport of analytes such as chemical and biological agents. Very large arrays, e.g., arrays of about $10^5$ supported biofunctionalized membranes are feasible. These arrays facilitate functional screening of membrane proteins and their interaction with libraries of the compounds of interest.

This platform forms the basis for a unique bioanalytical instrument that is capable of directly determining the activity of potential chemotherapy compounds with protein transducers such as P-glycoprotein at high throughput rates. This instrument permits screening of new and existing libraries of chemotherapy compounds for their biological activity without using expensive and indirect cell based assays. This instrument also facilitates the development of a fundamentally new approach to the characterization of membrane protein behavior. The central role that these proteins play in all aspects of cellular biology (e.g., cell signaling, cell motility, energy conversion, protein expression, cell division) cannot be over-emphasized. Further, the biofunctionalized membranes potentially have other biotechnological applications including: bioprocess separation; environmentally-responsive matrices (dermal patches, subcutaneous implants, etc) for drug delivery under feedback control; chemical and biological agent detection; and hazardous agent decontamination.

The bioanalytical device of the invention includes a biofunctional component and, optionally, a sensor component. The biofunctional component includes a membrane film, a protein transducer directionally oriented within the membrane film, and a support substrate in fluid communication with the membrane film and defining an aqueous compartment between the membrane film and the support substrate. Optionally but preferably, the biofunctional component also includes a transducer orienting layer disposed between the membrane film and the support substrate. In a variety of alternative embodiments, one or more of the constituent components of the biofunctional component can be integrated so as to form a composite structure. For example, the biofunctionalized membrane film can be integrated within the support, thereby increasing membrane stability and facilitating membrane processing.

Figure 1:
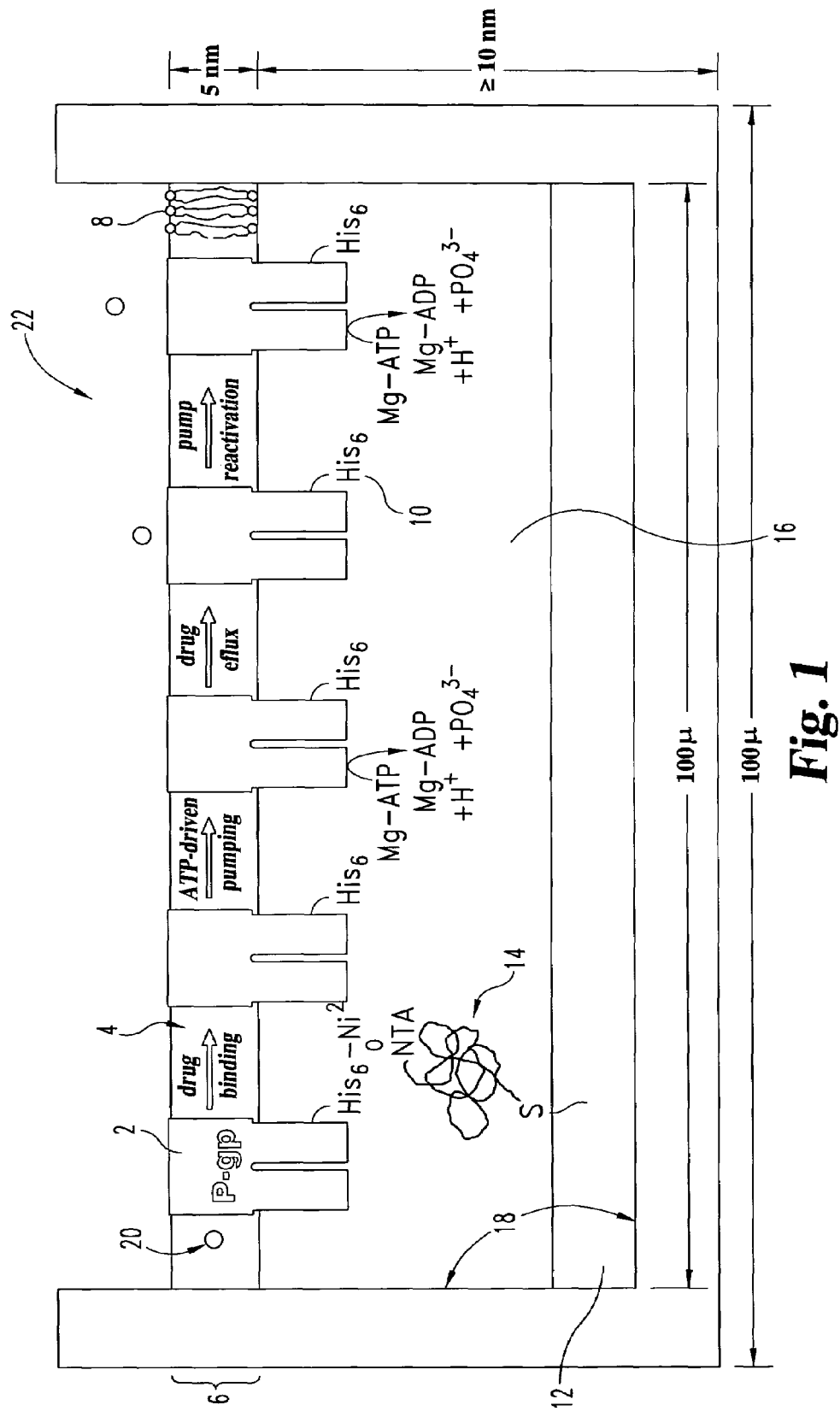
FIG. 1 is a cross-sectional view of a supported biofunctionalized membrane.

FIG. 1 presents a cross-sectional view of one illustrative embodiment of the biofunctional component of the device. Protein transducer 2, in this case P-gp, is embedded in membrane film 4 to yield biofunctionalized membrane 6. Bolalipids 8 are used to form the membrane film 4. Protein transducer 2 contains a $His_6$ tag 10 which allows tethering of the protein transducer 2 to a transducer orienting layer 12 using a polyethylene glycol (PEG) tether 14. Transducer orienting layer 12, which can be, for example, a hydrogel, contains a chemically responsive material, such as an environmentally sensitive dye. Inner aqueous compartment 16 is disposed between biofunctionalized membrane 6 and transducer orienting layer 12 and serves as a reservoir for substrate (in this embodiment, ATP) that drives the pumping action of protein transducer 2. Support substrate 18, which can include a gold, silicon or γ-alumina surface, for example, and is in this case formed from silicon, provides mechanical support for biofunctionalized membrane 6 and other device components and can also serve orienting and/or sensing functions. The mechanism pumping is depicted as a series of events (i.e. within the biofunctionalized membrane, moving from left to right) that produces a net analyte 20 flux from the inner aqueous compartment 16 to outer aqueous phase 22.

In a preferred embodiment, the protein transducer is P-glycoprotein (P-gp) and P-gp-mediated active drug transport is detected as a change in pH or ionic strength due to the coupled hydrolysis of ATP. Sensors developed from these asymmetric structures provide a direct indication of a drug candidate's susceptibility for P-gp pumping across the membrane, which will serve as a powerful tool for screening drug libraries for those leads that are likely to remain inside the target cell type, as discussed in more detail below. Discovery of novel compounds from high-throughput screening according to the present invention may lead to improved chemotherapeutic agents for refractory tumors.

The sensor component of the device, if present, detects a signal generated upon operation of the biofunctional component. The signal can be a chemical signal, an optical signal, an electrochemical signal, an electrical signal, an electromagnetic signal, or any other type of detectable signal. Typically, a signal generated by the device after application of a chemical reagent for analysis is indicative of the activity of the protein transducer. In embodiments containing both the biofunctional component and the sensor component, the biofunctional component is optionally but conveniently supplied as a replaceable cartridge, while the sensor component remains a permanent part of the device. It should be noted, however, that there are applications such as bioseparations wherein a sensing modality is not necessary.

The invention also includes a kit for making the biofunctional component of the bioanalytical device. The kit contains membrane film material, hydrogel precursors and a support substrate. Alternatively, the kit contains a preformed support substrate/transducer orienting layer, together with the membrane film material. Also included is packaging and instructions for use of the bioanalytical device for analysis of the activity of a membrane-embedded protein transducer. The kit allows the user to construct a membrane film embedded with a custom protein transducer of the user's own choosing.

Membrane Film

The membrane film can be formed from one or more natural or synthetic materials, such as lipids or other hydrophobic materials. Archaebacterial lipids from halophilic bacteria and Methanogen (i.e., any of the various archaebacteria (see Archaea) that produce methane; they include such genera as *Methanobacillus* and *Methanothrix*), and bacterial bolalipids from thermophilic bacteria are particularly useful. Other materials that can be used for the biomembrane film include, for example, non-fouling template-polymerized bilayers, bolaamphiphiles, triblock copolymers (such as PEG-PiB-PEG and PEO-PPO-PEO) and hydrogels. The membrane film is preferably planar. See, e.g., Salafsky et al., Biochemistry, 1996, 35, 14773-14781; Raguse et al., Langmuir, 1998, 14, 648-659; Groves et al., Langmuir, 2001, 17, 5129-5133; and Groves et al., Biophys. J., 1996, 71, 2716-2723; and U.S. Pat. No. 6,228,326, Boxer et al. for examples of supported membrane films. The use of synthetic lipids or lipid-like molecules allows the incorporation of structural modifications that can increase the stability of the supported membrane.

The membrane film can take the form of a bilayer, such as a lipid bilayer, or it can take the form of a monolayer structure. Naturally occurring lipids, with polar head groups and hydrophobic tails, typically form a bilayer. Boxer and coworkers have shown that supported membrane film arrays can be formed by liposome fusion with microcontact printed surfaces. Analysis of these films has revealed that the membrane bilayers retain their fluidity via entrapment of a nm-sized aqueous phase between the membrane coating and solid support. Proteoliposome fusion with solid supports has further shown that proteoliposome can fuse with acid-treated glass surfaces to give supported membranes with the membrane proteins oriented in a vectorial fashion. However, a feature common to supported bilayer membranes is their tendency to delaminate from the solid support within 24 hours.

Accordingly, a monolayer structure is preferred for the membrane film of the biofunctional component of the device. A monolayer structure can be formed from, for example, bolalipids, bolaamphiphiles, or amphiphilic triblock copolymers. Supported bolalipid membranes are especially preferred. Optionally, lipid components of the membrane can be tethered to the support substrate (e.g., Cornell et al., *Nature*, 1997, 387:580-583.)

Biofunctionalization of the Membrane Film

Embedded within the membrane film are directionally oriented membrane-spanning proteins that function as molecular transporters ("protein transducers"), yielding a "biofunctionalized membrane." The biofunctionalized membrane can be considered a biomimetic structure. It functions as an active transport layer, such that analytes can be actively transported across it via the protein transducers.

Protein Transducers

The invention is not limited to the use of any particular protein transducer, any membrane protein that can function as a molecular transporter across the membrane film can be used in the biofunctionalized membrane. It should be noted that the bioanalytical device is equally suitable in applications involving efflux of an analyte or uptake of an analyte, depending on the bioactivity of the protein transducer selected. Examples of protein transducers than can be used in the present technology include proteins associated with multi-drug resistance such as the product of the human MDR1 gene, P-glycoprotein (including MDR efflux pump, peptide efflux pump and phospholipid flippase), the product of the human BSEP gene, the bile salt export pump (both members of the APT-binding cassette superfamily, described below) and other multi-drug resistance-associated proteins (MRPs), mitoxantrone-resistance proteins (MXR1/BCRP/ABCP/ABSG2), and porins. Another example is cyt bc, a complex of cytochrome b and c. ATP synthase can be driven by the $H^+$ gradient generated by co-immobilized cyt bc complex.

ABC transporters. The ATP-binding cassette (ABC) superfamily contains both uptake and efflux transport systems. ATP hydrolysis, typically without protein phosphorylation, energizes transport. There are dozens of families within the ABC superfamily, and family generally correlates with substrate specificity. The transporters of the ABC superfamily consist of two integral membrane domains/proteins and two cytoplasmic domains/proteins. The uptake systems (but not the efflux systems) additionally possess extracytoplasmic solute-binding receptors. Both the integral membrane channel constituent(s) and the cytoplasmic ATP-hydrolyzing constituent(s) may be present as homodimers or heterodimers.

The superfamily includes prokaryotic ABC-type uptake transporter families including, without limitation: Carbohydrate Uptake Transporter-1 (CUT1); Carbohydrate Uptake Transporter-2 (CUT2); Polar Amino Acid Uptake Transporter (PAAT); Hydrophobic Amino Acid Uptake Transporter (HAAT); Peptide/Opine/Nickel Uptake Transporter (PepT); Sulfate Uptake Transporter (SulT); Phosphate Uptake Transporter (PhoT); Molybdate Uptake Transporter (MolT); Phosphonate Uptake Transporter (PhnT); Ferric Iron Uptake Transporter (FeT); Polyamine/Opine/Phosphonate Uptake Transporter (POPT); Quaternary Amine Uptake Transporter (QAT); Vitamin $B_{12}$ Uptake Transporter ($VB_{12}T$); Chelate Uptake Transporter (FeCT); Manganese/Zinc/iron Chelate Uptake Transporter (MZT); Nitrate/Nitrite/Cyanate Uptake Transporter (NitT); Taurine Uptake Transporter (TauT); Putative Cobalt Uptake Transporter (CoT); Thiamin Uptake Transporter (ThiT); and Brachyspira Iron Transporter (BIT).

The superfamily includes bacterial ABC-type efflux transporter families including, without limitation: Capsular Polysaccharide Exporter (CPSE); Lipooligosaccharide Exporter (LOSE); Lipopolysaccharide Exporter (LPSE); Teichoic Acid Exporter (TAE); Drug Exporter-1 (DrugE1); Putative Lipid A Exporter (LipidE); Putative Heme Exporter (HemeE); β-Glucan Exporter (GlucanE); Protein-1 Exporter (Prot1E); Protein-2 Exporter (Prot2E); Peptide-1 Exporter (Pep1E); Peptide-2 Exporter (Pep2E); Peptide-3 Exporter (Pep3E); Probable Glycolipid Exporter (DevE); $Na^+$ Exporter (NatE); Microcin B17 Exporter (McbE); Drug Exporter-2 (DrugE2); Microcin J25 Exporter (McjD); Drug/Siderophore Exporter-3 (DrugE3); Putative Drug Resistance ATPase-1 (DrugRA1); and Putative Drug Resistance ATPase-2 (DrugRA2).

The superfamily also includes other ABC-type efflux transporter families, mostly eukaryotic, including, without limitation: Multidrug Resistance Exporter (MDR) (includes P-glycoprotein); Cystic Fibrosis Transmembrane Conductance Exporter (CFTR); Peroxysomal Fatty Acyl CoA Transporter (FAT); Eye Pigment Precursor Transporter (EPP); Pleiotropic Drug Resistance (PDR); α-Factor Sex Pheromone Exporter (Ste); Conjugate Transporter-1 (CT1); Conjugate Transporter-2 (CT2); MHC Peptide Transporter (TAP); Heavy Metal Transporter (HMT); Cholesterol/Phospholipid/Retinal (CPR) Flippase; and Mitochondrial Fe/S Protein Exporter (MPE).

Human ATP-Binding cassette transporters number about 48 (see http://nutrigene.4t.com/humanabc.htm) and include the ABC1 family (subfamily ABCA), MDR family (subfamily ABCB), MPR family (subfamily ABCC), ALD family (subfamily ABCD), OABP family (subfamily ABCE) GCN20 family (subfamily ABCF) and White family (subfamily ABCG). For a review yeast ABC transporters, see Taglicht et al., *Meth. Enzymol*. 1998, 292:130-162.

P-glycoprotein. The successful treatment of metastatic and disseminated cancer is to a large degree dependent upon the effectiveness of cytotoxic anticancer drugs. Some commonly used chemotherapeutic agents are the Vinca alkaloids, the anthracyclines, the epipodophyllotoxins, taxol, and actinomycin D. Although these natural product compounds share little to none of the same chemistry, they all are amphipathic molecules with planar aromatic rings that preferentially partition into organic solvents. Unfortunately, most cancers either are intrinsically resistant to any initial treatment with these therapeutic compounds or acquire resistance to a broad spectrum of these agents over time (Gottesman et al., *Annu. Rev. Biochem*. 62, 385 (1993)).

It is well established that this broad-based resistance results, in large part but not solely, from the overexpression of a 170 kDa plasma membrane polypeptide known as the multidrug transporter or P-glycoprotein (P-gp), encoded by the multidrug resistance MDR1 gene in humans (Gottesman et al., *Annu. Rev. Genet*. 29, 607 (1995)). P-gp is a member of the ATP binding cassette (ABC) superfamily of membrane transporters, with toxin binding domains localized within the transmembrane regions. It is an energy-dependent multidrug transporter that reduces the accumulation of an extremely broad range of structurally unrelated hydrophobic and amphipathic molecules within cells. P-gp is known to efflux cytotoxic drugs out of cells and limit the influx of drugs into cells. Known substrates include vinblastine, daunomycin, actinomycin D, taxol, colchicine, verapamil and rapamycin.

P-gp is believed to play a protective barrier role in normal tissues, defending them from the damaging effects of toxins, dietary drugs and other harmful environmental agents. However, because it plays a major role in drug resistance, P-gp is making it the subject of intense interest to the pharmaceutical community. Many different human cancers express the MDR1 gene at levels sufficient to confer multidrug resistance. Based on an analysis of several hundred different human cancers, it can be estimated that approximately 50% of human cancers will express the MDR1 gene at some time during therapy (Ambudkar et al., *Annu. Rev. Pharmacol. Toxicol*. 39, 361 (1999)). The World Health Organization has also estimated that multidrug resistant bacteria account for near 60% of all hospital-acquired infections. The major therapeutic challenge of multidrug resistance in cancer and infectious disease clearly illustrates why there are large drug discovery efforts at major pharmaceutical companies that are directed toward this problem. Thus, although there are many membrane proteins of interest, P-glycoprotein (P-gp) is preferred for use in the biofunctionalized membranes of the invention due to the important role it is thought to play in broad-based resistance to chemotherapies.

Figure 2:
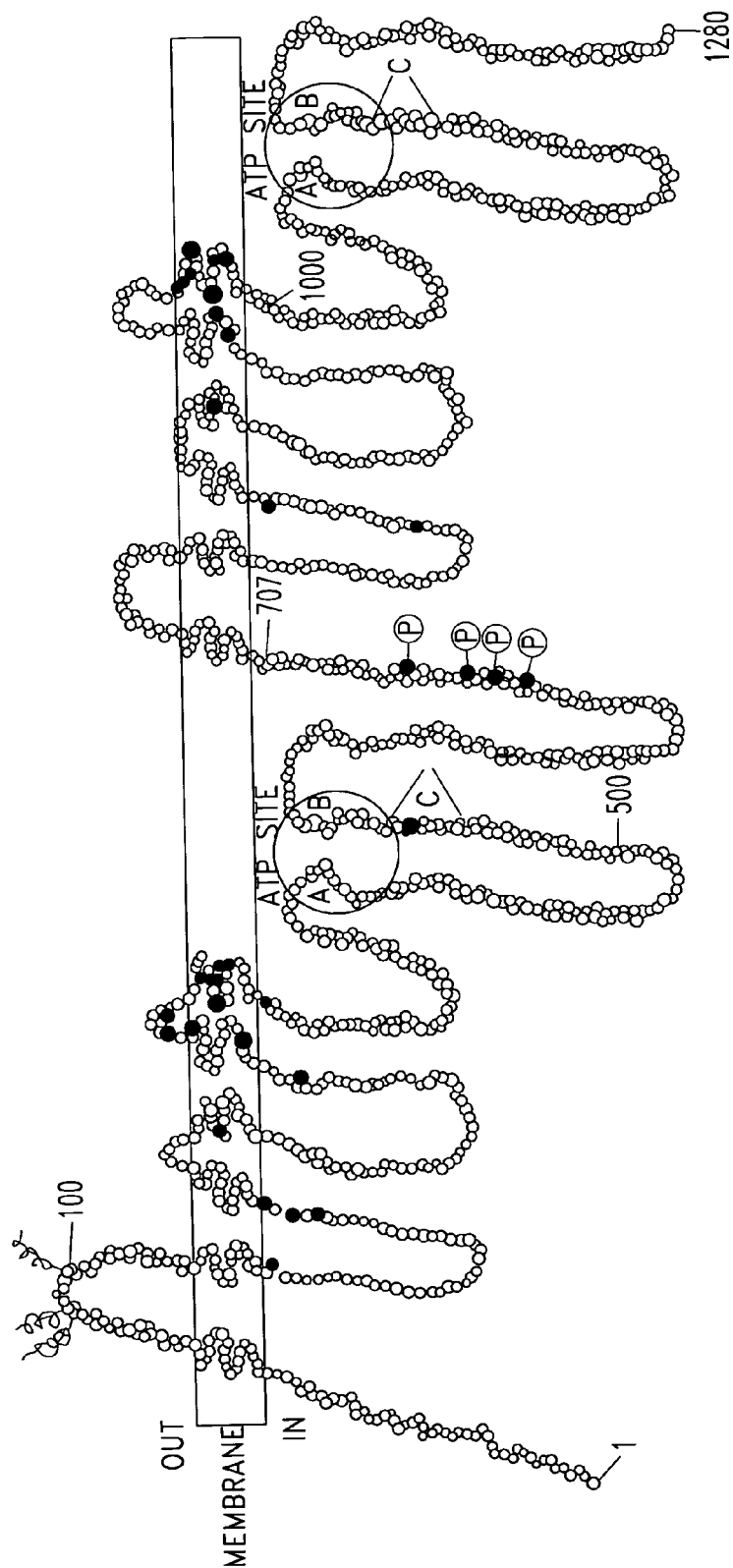
FIG. 2 is a two-dimensional hypothetical model of human P-glycoprotein (P-gp) structure based on hydropathy plot analysis of primary amino acid sequence. The ATP binding/utilization domains are circled with the Walker A, B and "linker dodecapeptide" or "signature sequence" (LSGGQ) motifs are designated by the letters "A", "B" and "C." Putative glycosylation sites are represented by squiggly lines. Serine residues known to be phosphorylated are shown as dark circles with an attached and encircled "P". The filled-in circles show many of the positions of mutations that change substrate specificity in human P-gp.

Human P-gp is an integral membrane protein comprised of two homologous halves each thought to span the plasma membrane bilayer six times with each half containing an ATP binding site (Gottesman et al., *Annu. Rev. Genet*. 29, 607 (1995)). (FIG. 2). Topology studies reveal that both the amino and carboxyl termini of P-gp are located in the interior of the cell. The drug binding sites are localized to the transmembrane domains of the transporter (Greenberger, *J. Biol. Chem.* 268, 11417 (1993); and Bruggemann et al., *J. Biol. Chem.* 267, 21020 (1992)) whereas the ATP sites are cytosolic. Hydrolysis of adenosine triphosphate (ATP) on the cytosolic surface of the membrane is coupled to the transport of substrate molecules out of the cell, which means that active transport is coupled to energy consumption and local pH.

ATP binding and hydrolysis are essential for the proper functioning of P-glycoprotein, including drug transport (Horio et al., *Proc. Natl. Acad. Sci. USA* 85, 3580 (1988)), however, how the energy of ATP hydrolysis is transduced to transport this large variety of hydrophobic agents out of the plasma membrane or the cytoplasm into the extracellular milieu remains unknown. One proposed model is that P-gp may reduce intracellular drug concentrations by acting as a "hydrophobic vacuum cleaner" effectively increasing drug efflux and decreasing drug influx by the recognition and removal of compounds from the membrane before they reach the cytosol to elicit their cytotoxic effects (Raviv et al., *J. Biol. Chem.* 265, 3975 (1990)). The major sites of interaction of several P-gp inhibitors and substrates have been localized to transmembrane regions 5, 6, 11 and 12 as determined by photoaffinity labeling, digestion with proteases or cyanogen bromide, and specific immunoprecipitation with antibodies directed against polypeptide epitopes of P-gp. Additionally, one of the most useful and informative experimental approaches used to probe substrate specificity has involved the study of mutant and chimeric molecules that are either naturally occurring or artificially engineered. Many of these mutations in human P-gp molecule affect changes in the drug specificity of the transporter relative to the wild-type molecule. These mutations are found scattered throughout the molecule but are generally localized to the transmembrane regions with most of the functionally relevant mutations found in transmembrane domains 5, 6, 11 and 12.

Because multidrug resistance has proven to be an enormous clinical problem, there is great interest in both academic and industrial laboratories in the development of novel and clinically useful therapeutic agents to serve as P-gp substrates and inhibitors. These compounds could be used to facilitate the treatment of human cancers as well as serve as diagnostic agents for the non-invasive evaluation of P-gp expression in certain tumors. With the advent of combinatorial chemistry methodologies, large numbers of these compounds can be generated. At present, however, there are no rapid ways to screen large numbers of these compounds for activity. Existing vesicle and cell-based assays for analyzing human P-gp activity are slow and difficult to adapt to high throughput methods. There is a clear need for rapid, high throughput methods to screen combinatorial libraries of P-gp chemosensitizers and substrates.

The present invention provides medium and high-throughput methods for screening potential new P-gp substrates and modulators. The invention is exemplified by arrays of human P-glycoprotein (P-gp)-functionalized asymmetric membranes. Arrays constructed from the biofunctionalized membrane structures can be used to identify promising pharmaceutical compounds and fingerprint unknown environmental toxins based on P-gp activity patterns.

Specific domains of P-gp involved in substrate recognition have recently been identified; mutational studies further indicate that it will be possible to engineer designer transporters that would selectively discriminate between molecular species. The present invention envisions a broad range of active transport membrane structures that are constructed based on the same operating principles, but differing in their molecular transport specificity.

A particularly promising application of P-gp is as a transducing element for energy coupled transport in biofunctionalized membrane constructs. Genetically engineered designer transporters that recognize specified classes of substrate molecules can be realized in sensor arrays constructed from such materials. These devices are useful in a wide variety of applications, including: first-line rapid screening of large drug libraries in high throughput fashion, characterization of the pumping mechanism of P-gp, or fingerprinting unknown environmental toxins and functionally-related classes of pharmacological agents based on P-gp activity patterns.

Figure 3:
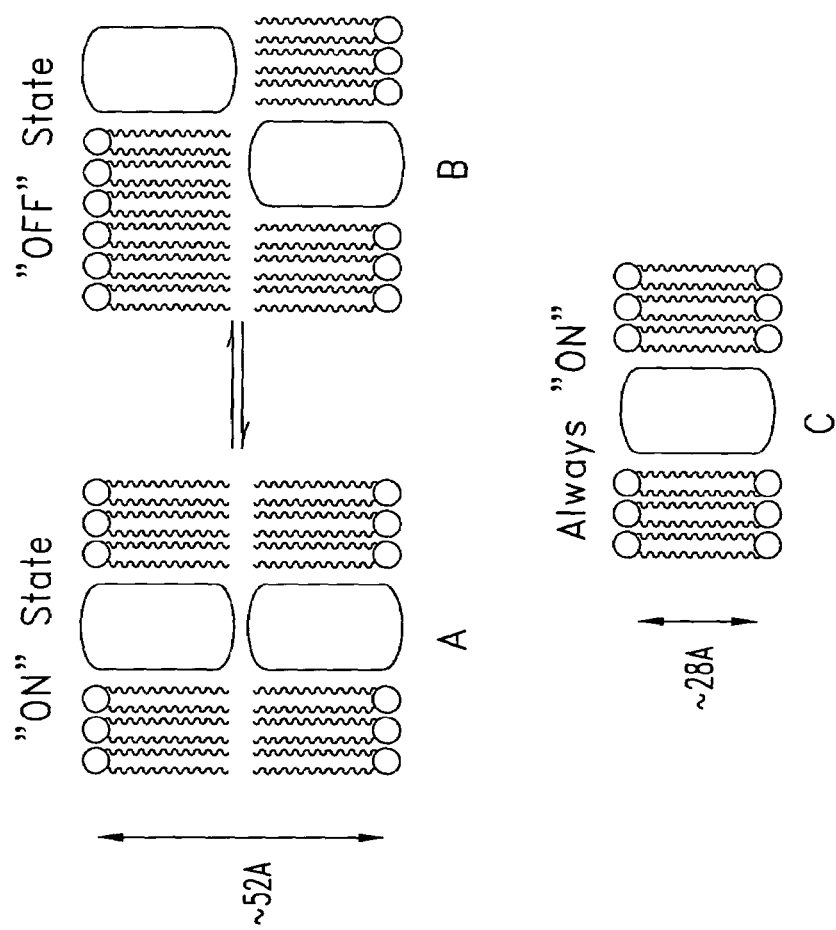
FIG. 3 is a schematic representation of (A) gramicidin in a bilayer membrane in the "on" state; (B) gramicidin in a bilayer membrane in the "off" state; and (C) gramicidin in a bolalipid monolayer membrane.

Gramicidin. Gramicidins are known to increase the permeability of biological membranes to protons and alkali-metal cations by forming transient dimeric ionophoric channels through the membrane, and are useful as protein transducers in the present invention. In a bilayer, gramicidin cycles between "on" and "off" states as the monomers move within the fluid membrane (FIGS. 3A and B). Alternatively, in the biofunctional membrane of the present invention, gramicidin can placed be in a perpetually "on" state by embedding it into a monolayer membrane (FIG. 3C). In a monolayer, only a monomer of gramicidin is needed to allow passage of analytes through the membrane.

Orientation of the Protein Transducers within the Biofunctionalized Membrane

The invention is not limited by the method used to orient the protein transducers within the membrane film. Many orientation strategies rely on the concept of "tethering" the protein to a component of the transducer orienting layer, if present, or directly to a component of the support substrate.

Methods for orienting the protein transducers in the membrane film range from the very specific to the relatively nonspecific. Specific ligand/receptor interactions such as biotin-streptavidin can be utilized, or the proteins can incorporate His-, Myc-, FLAG- or HA-affinity tags. A polyhistidine-$Ni^{2+}$-NTA (or IDA) binding interaction is especially useful. The proteins can be engineered to contain epitopes or antigens that bind an antibody present in the transducer orienting layer or as part of the support substrate. Orientation can be achieved by taking advantage of ligand binding sites (e.g., ATP binding sites) or sites of metal chelation either present in the naturally occurring protein or engineered into it. Protein-, carbohydrate- or lipid-nucleic acid chimeras can be used, thereby allowing the formation of DNA duplexes via hybridization with complementary nucleic acids present within the transducer orienting layer or on the surface of a DNA-modified support substrate. Covalent reactions with thiols or amines are another option for orienting the proteins within the membrane layer. As a less specific method, charge clusters can be used to orient the protein transducer using electrostatic interactions, such as electrostatic adsorption onto a charged surface. Oligonucleotide-lipid conjugates, DNA aptamers, inclusion complexes with cyclodextrin monolayers, and/or microcontact-printed thiols on hydrogel supports, are further examples of methods that can be used to fix the orientation of the protein transducers and provide mechanical support.

In embodiments of the device that include a transducer orienting layer, it is typically composed primarily a polymeric layer such as a hydrogel layer, a sol-hydrogel layer or composite sol-hydrogel layer. Functionalities important for tethering the protein transducers can be integrated into the polymeric layer either covalently or noncovalently. The hydrogel is typically formed from cross-linked polymers. However, the invention is not limited by the nature of the materials used to make the transducer orienting layer.

The technique used to "tether" the protein transducer is preferably one that allows the requisite amount of membrane fluidity. Fluidity is important so that the proteins can move within the membrane. Fluidity can be achieved in a number of different ways. The interaction between the protein and the tethering component in the transducer orienting layer or the support substrate may be strong, yet reversible. For example, the transducer orienting layer can take the form of a cyclodextrin film, and the protein transducer (derivatized or engineered to contain a hydrophobic inclusion ligand at the end of the tether) can reversibly bind the cyclodextrin to form an inclusion layer. Alternatively, the interaction the protein and the tethering component may be covalent and essentially irreversible, but the tethering component is able to move within the transducer orienting layer, as in a hydrogel layer, a sol-hydrogel layer or composite sol-hydrogel layer.

Figure 4:
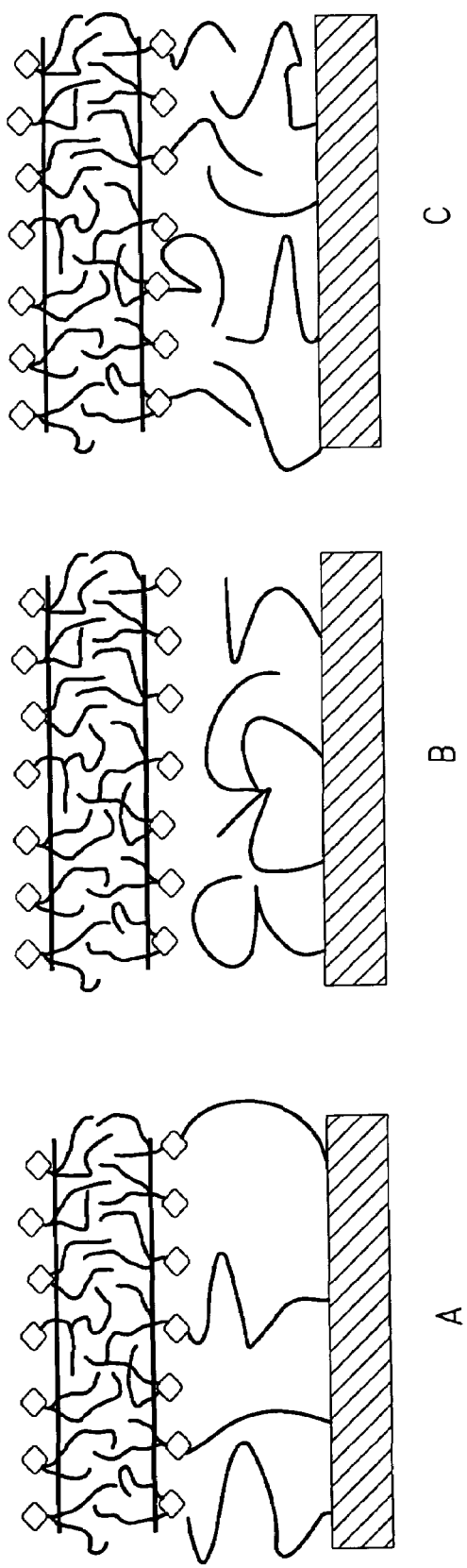
FIG. 4 is a schematic representation of different supported membrane configurations: (A) PEG chains attached to both the support and the membrane; (b) PEG chains only attached to the solid support; and (c) PEG chains grafted to one material, either the support or the membrane.

There are at least three possible ways to design the polymeric transducer orienting layer, such as a PEG layer, to avoid direct contact between the biofunctionalized membrane and the underlying support substrate (FIG. 4). In FIG. 4A, the PEG molecules are chemically bound to both the support and the membrane. FIG. 4B depicts the case where PEG is chemically bound to the support, but not the lipid membrane. The polymer layer repels the membrane, leading to a supported membrane on top of the extended PEG layer. The third case, FIG. 4C, corresponds to the situation where PEG units are grafted single surfaces, either the lipid membrane or membrane support. Theoretical calculations shows that when PEG is chemically bound to both the membrane and support, a much sharper energy minimum is observed for these interactions, suggesting that this approach may be a preferred way to support the biofunctionalized membrane at the energetically-favorable distance of choice.

It may be desirable to provide additional room between the membrane and support for effective function of the protein transducer. This can be achieved by using a softer interaction. For example, for some polymers attaching polymers of half chain length to each surface theoretically results in interactions that are similar in magnitude as the case with only single point attachments.

The transducer orienting layer can contain molecules having detector moieties, such as dye molecules to detect, for example, ATP hydrolysis, which is indicative of molecular transport through the membrane embedded protein transducer; it can also contain molecules having orienting moieties such as polymers that function to orient the membrane-embedded protein transducers within the membrane film.

Support Substrate

The support substrate provides mechanical support for the biofunctionalized membrane. It is not limited by the type of material used for fabrication. For example, in one embodiment the support substrate can be a nanoporous structure; in other embodiments it can be a solid. Suitable materials for use in fabricating the support substrate include anodic γ-alumina or nanoporous silica structures. It can also take the form of a glass, gold (Au), an Au electrode, or an indium tin oxide (ITO) electrode.

The transducer orienting layer and support substrate can be distinct layers, or they can be integrated. In some embodiments, a single layer composed of, for example, cross-linked polymers with dyes and orienting molecules covalently attached, can function as both the support and the transducer orienting layer.

Additional Structural Considerations

If desired, the distance between the biofunctionalized membrane and the hydrogel/support substrate support layer(s) can be controlled by the use of water soluble polymers, such as oligo(ethylene glycol) spacer units, that extend between the biofunctionalized membrane and the transducer orienting layer/support substrate, tethering them together and acting somewhat like the springs of a mattress underlying the biofunctionalized membrane. X-ray reflectivity and x-ray standing wave measurements can be used to precisely determine this distance.

In an alternative embodiment, the transducer orienting layer/support substrate layer(s) are replaced by a planar gold electrode, and the transport of charged analytes is detected electrochemically.

Microfabrication Technologies for the Support Substrate and Transducer Orienting Layer The biofunctional membranes are oriented in the devices and supported to provide transport directionality and mechanical stability. Support is provided by a substrate, and a transducer orienting layer, such as a sol-gel matrix, is optionally added to the surface of the support substrate to assist in orienting the membrane proteins and provide optically addressable groups for the transduction of local changes in the chemical environment.

In recent years, there has been a merger of microelectronics and biological sciences to develop "biochip" devices. The term biochip has been used in various contexts, but can be generally defined as a micro-fabricated device that is used for processing (delivery, processing, and analysis) of biological species (molecules, cells, etc.). Asymmetric supported P-gp membrane arrays can be formed on the surface of 100×100 micron reaction wells that will allow rapid screening of up to 100,000 distinct combinations of membrane protein-drug candidate. These arrays can be assembled by microfabricating reaction chambers from Si (100) wafers using standard bulk micromachining techniques. Surface chemistries can then be used to orient P-gp and the host lipid membrane in the reaction chambers.

The device can be conveniently assembled in stages. Initially, for example, a hydrogel precursor solution can be added via ink jet head to the support. Then a gellating agent can be added, again via ink jet head, to cause gellation of the hydrogel precursors. To this is added the protein transducer (for example, as a detergent micelle solution), followed by the membrane film material (as a vesicle solution that also contains ATP as a solute) to yield the biofunctionalized structure. As noted herein, the transducer orienting layer can be overlaid on the support substrate, or integrated within it.

The use of a support allows both the outer surface (akin to the extracellular surface) or inner surface (akin to the cytosolic surface) of the biofunctionalized membrane to be addressed (FIG. 1). The inner surface is in contact with the aqueous compartment that contains the entrapped aqueous solution. The outer surface of the membrane can be addressed by addition of reagents that potentially activate P-gp function; the inner surface can be addressed—albeit slowly—by sampling the solution residing within the hydrogel support. For example, if ATP is hydrolyzed, its reaction products will slowly infuse throughout the water-filled voids of the hydrogel. Since ATP and its hydrolysis products are confined within a compartment bounded by the membrane film and the container walls, these agents have no other option but to diffuse away from the membrane. Sampling of this aqueous environment and analysis by mass spectrometry, scintillation, and the like can then be used to detect the extent of ATP hydrolysis. Fabrication of the biofunctionalized structures on planar substrates utilizes common membrane protein purification techniques, such as decylglucoside micellar solubilization combined with surface binding and orientation using molecular recognition elements such as histidine- or myc-tags (see below).

Existing nanoporous materials (e.g. anodic γ-alumina) represent suitable hosts. Second-generation materials, such as self-assembled nanoporous silica structures (e.g., SBA-15) created using templates formed by the self-assembly of amphiphilic triblock copolymers (Yang et al., *Science* 282, 2244-2246 (1998)) are also envisioned to allow further integration of the biofunctionalized membrane into the nanoporous support to increase membrane stability and facilitate membrane processing. In a preferred embodiment, nanoporous alumina membranes are used to support the biofunctional membranes. The nanoporous membranes are ideally suited for incorporation in the devices because they have highly uniform pores of size 20-100 nm, a high elastic modulus, and can withstand high temperatures. Standard wafer bonding techniques can be used to bond the silicon wafers to the membrane. After the silicon-nanoporous membrane is assembled, inkjet printing can be used to deliver the sol-gel precursors to the active surface of the membrane, followed by photochemical or thermal gellation of the material.

The transducer orienting layer can serve one or more of the following functions: 1) as a mechanical support matrix, 2) as a scaffold for displaying specific affinity elements that promotes protein immobilization within the biofunctionalized membrane such that the cytoplasmically accessible ABC sites (i.e. the ATP hydrolysis domains) are oriented toward the substrate, 3) as a matrix within which pH-sensitive or ion-specific dyes can be immobilized (by modifying the hydrogel with commercially-available, isothiocyanate forms of the dye) to enable rapid, highly sensitive optical detection of the environment near the ABC sites, and 4) when structurally integrated with the substrate or serving dual functions as transducer orienting layer and substrate, as a nanoporous substrate that allows reagent access to both surfaces of the protein-embedded membrane, a level of control that no other membrane-based technique can offer.

Microreaction chambers can also be constructed from bulk micromachined structures and nanoporous membranes. Asymmetric biofunctional membranes can be provided on the micron scale in arrays of at least 100,000 distinct combinations of membrane protein-drug candidate compound. Microreaction chambers (eg., 10×10 µm² reaction chambers) can be fabricated with sol-gel—substrate supports at a density of 100,000 chambers/cm². Formation of distinctly addressable arrays is based on the ability to dispense $10^{-15}$ liter volumes using inkjet dispensing technologies (see below), and construct reaction chambers in which these fluids can be dispensed on durable biofunctionalized membranes that have been assembled on nanoporous supports.

Figure 5:
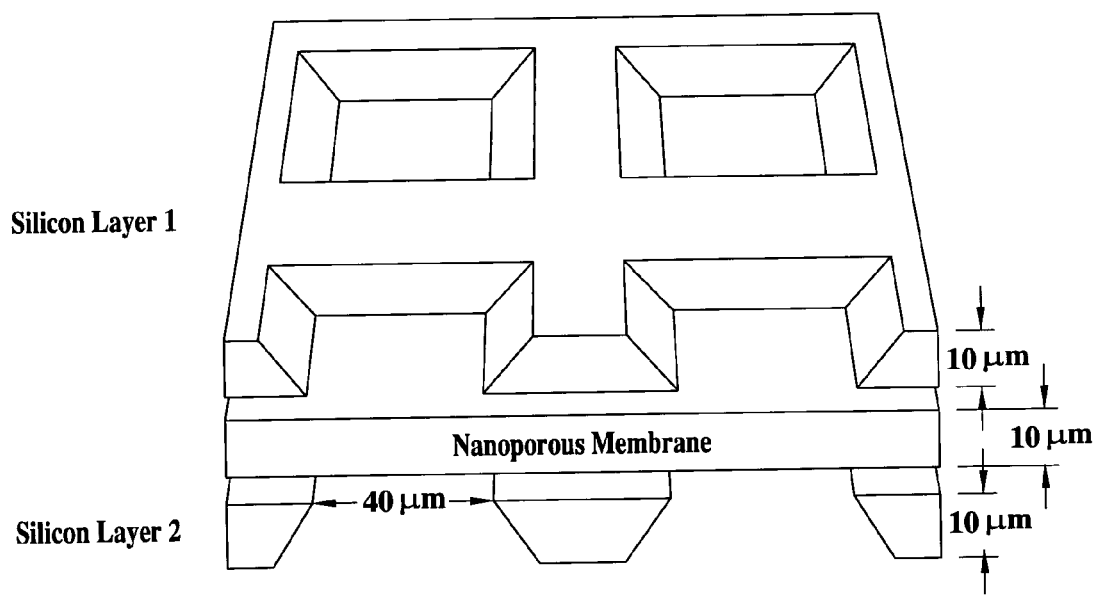
FIG. 5 is a schematic representation of three elements used to construct the microreactor arrays.

The reaction chambers can be assembled by microfabricating grid like structures from silicon and fusing them with the nanoporous support. FIG. 5 shows how the two grids and nanoporous support can be assembled. The reaction chambers themselves can be machined from a Si (100) wafer using standard bulk micromachining techniques (Petersen, *Proc. IEEE* 70, 420-457 (1982)). These layers serve to localize the solutions are be delivered through microfluidic means. Surface chemistries, e.g., silane or thiol monolayers, are used to control adsorption of proteins and lipids in the reaction chambers. Protein and membrane chemistries that are compatible with the "ink jet" technologies are preferred for use in constructing the addressable, oriented arrays of the invention.

Design and synthesis of membrane materials for the biofunctionalized membrane. Two competing physical chemical issues impact the function and ruggedness of the biofunctionalized membrane-based device—membrane fluidity and mechanical stability. Membrane fluidity is required for function of membrane proteins. The membrane materials used for immobilization of the membrane proteins are therefore preferably in their liquid crystalline phase at the operating temperature of the device (i.e. pumping activity may be lost if the host membrane material is in the gel phase).

Even though the membrane fluidity can be controlled experimentally by controlling temperature, it is undesirable to use this approach, since the thermal stability of physiologically active proteins such as P-gp may be limited above physiological temperatures (37° C.). The low temperature limit of the proposed device, which contains aqueous reagent compartments, is near 0° C. This narrow temperature range for device operation places stringent demands on the structure and composition of the host membrane material.

Preferred materials are naturally occurring or synthetic lipid compounds that have the ability to form stable membranes with low intrinsic permeabilities toward the substrate, for example ATP, a substrate for P-gp. Synthetic materials can be used as dopants within the membranes formed by natural materials. In addition, since the functional devices undergo multiple reagent and analyte addition steps, the membrane material also needs to be physically robust.

It is known that supported membrane film arrays can be formed by fusion of liposomes with microcontact printed surfaces. Analysis of these films has revealed that the membrane bilayers retain their fluidity via entrapment of a nm-sized aqueous phase between the membrane coating and solid support. Proteoliposome fusion with solid supports has also been shown to yield supported membranes with photosynthetic reaction centers oriented in a vectorial fashion. Most of the known methods for stabilizing membranes involve polymerization of vinylic lipid monomers within the bilayer. Unfortunately, in the past this approach has always led to loss of membrane protein activity, either through loss of membrane fluidity or via direct protein-monomer reactions.

Figure 6:
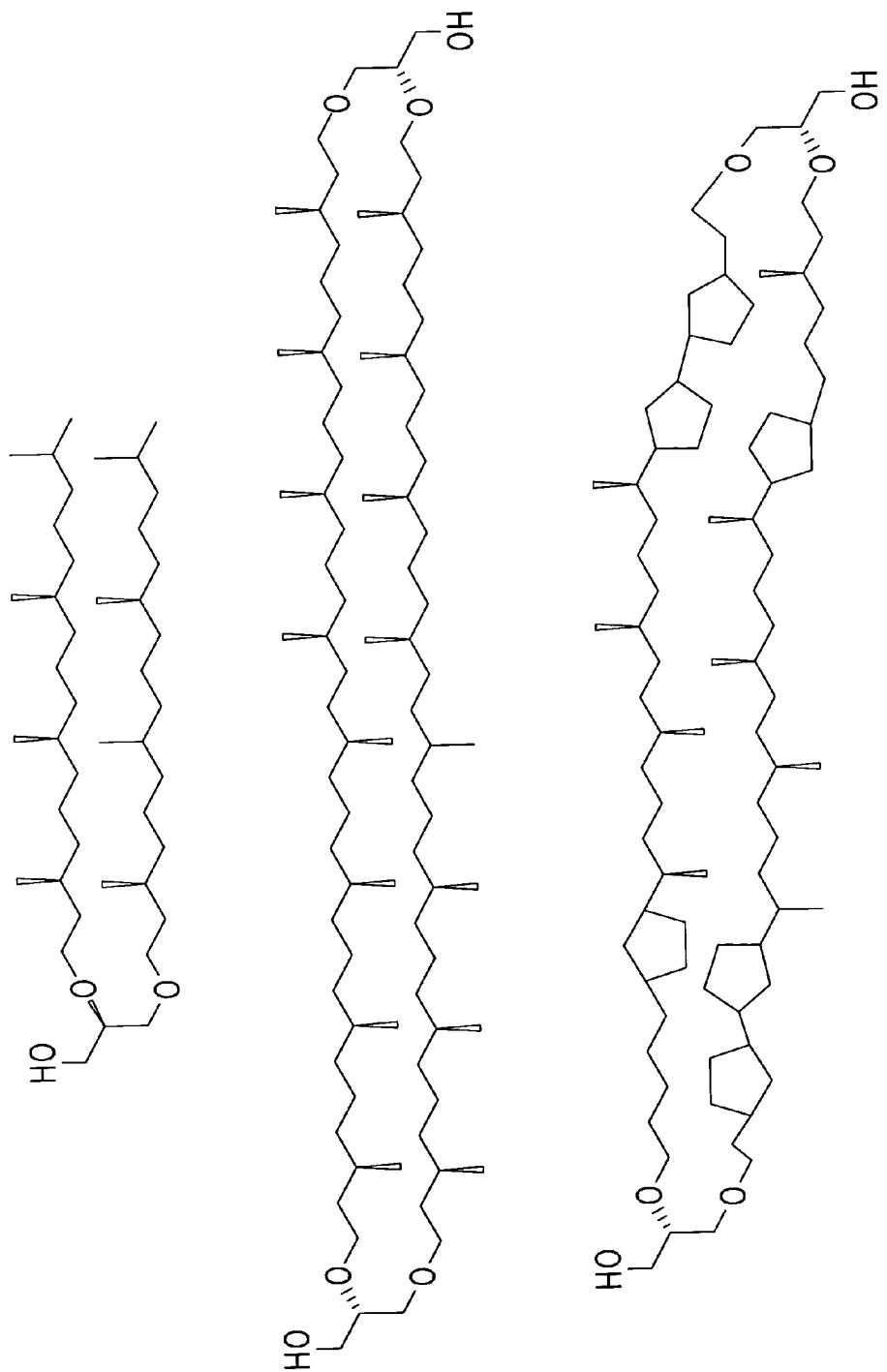
FIG. 6 shows the structures of naturally occurring bolalipids isolated from thermophilic archaebacteria.
Figure 7:
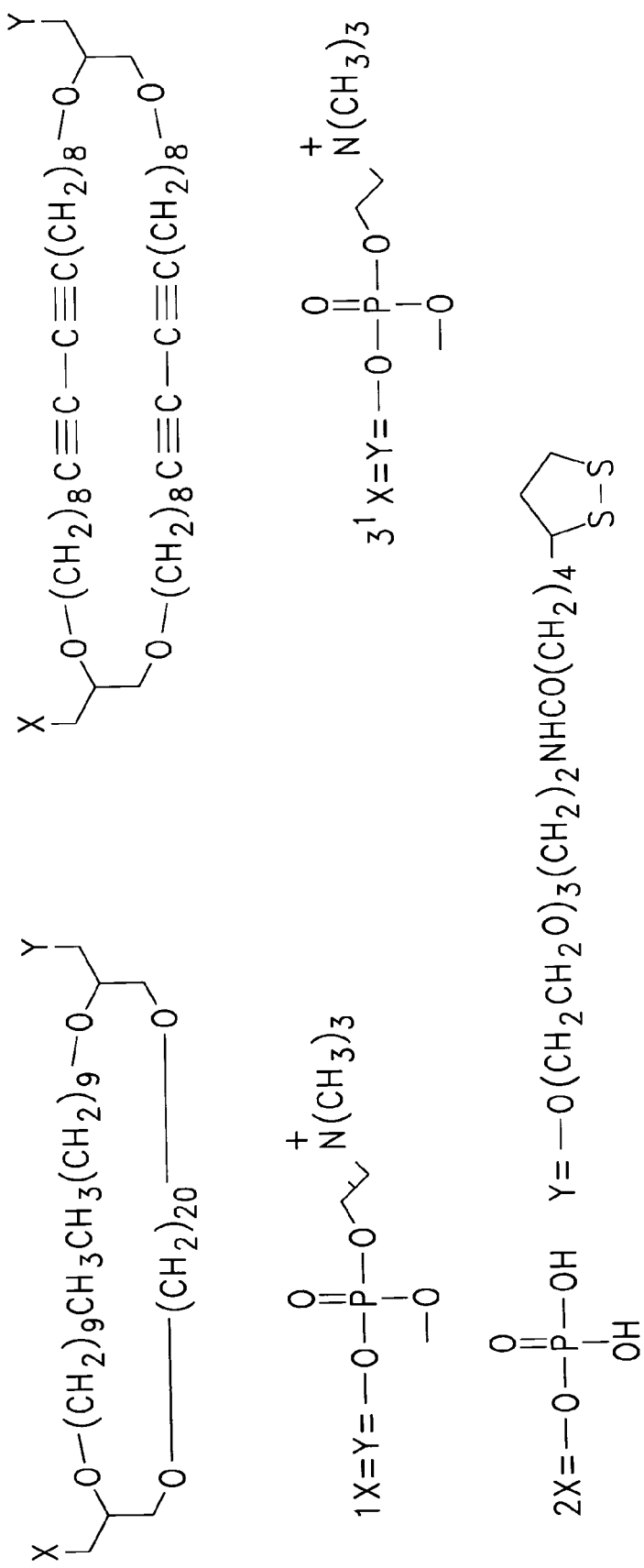
FIG. 7 shows representative synthetic bolalipids that form stabilized supported membranes.

The apparently mutually-incompatible material demands of membrane fluidity and mechanical stability can be resolved by, for example, using bolalipid materials such as bolaamphiphiles that are tethered to an underlying polymeric scaffold. Bolalipids are a family of natural and synthetic bipolar membrane lipids that are patterned after the membrane materials found in the extremely thermophilic organisms such as *Sutfolobus acidocaldarius*, that thrive under conditions as harsh as pH 1 and ≧100° C. *S. acidocaldarius* cell membranes consist of components derived from unique glyceryl tetraether lipids often bearing two polar headgroups and isoprenyl-based or cyclopentane ring-modified membrane spanning alkyl chains that connect the two headgroups together, and acyclic and macrocyclic structures (FIG. 6). Representative synthetic bolalipids are shown in FIG. 7.

Bolalipids preferentially form aqueous dispersions with very little curvature of the membrane due to their centrosymmetric molecular structures (e.g. 1 and 3 in FIG. 7) and preferential placement of one polar headgroup at each interface of the bolamembrane (i.e. an elongated, rather than U-shaped, conformation is the predominant orientation). Recent pulsed field gradient NMR experiments indicate that the diffusion coefficient of these lipids is more than two orders of magnitude slower than the lateral diffusion rate of conventional monopolar lipids. This observation, taken together with the cross-fracturing behavior seen in freeze-fracture TEM and the highly ordered Raman spectra of these membranes, is consistent with the occurrence of an elongated, transmembrane conformation of these lipids. This is expected to significant impact the stability of supported membranes formed from these materials.

The unusual stability of these lipids is attributed to their resistance toward hydrolysis (due to the chemically robust ether linkage) and delamination (due to the presence of membrane-spanning alkyl chains, a chemical architecture that effectively "crosslinks" the membrane in a direction normal to the membrane surface). These features have been incorporated within a series of bolalipids containing $C_{16}$- and $C_{20}$-based transmembrane chains that have been synthesized and found to possess exceptional membrane stability relative to conventional bilayer membrane materials (Patwardhan et al., *Org. Lett.* 1, 241 1999; DiMeglio et al., *Langrmuir* 16, 128 (2000); and Patwardhan et al., *Langmuir* 16, 10340 (2000)).

Figure 8:
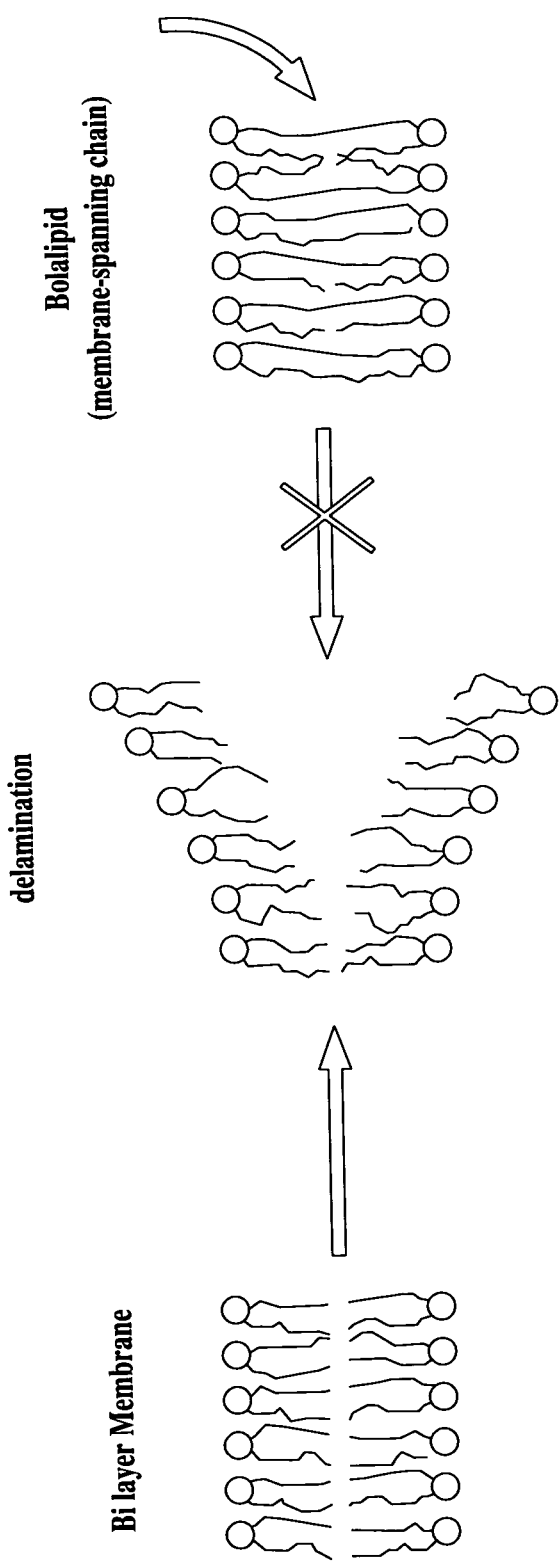
FIG. 8 shows the delamination process for bilayer membranes.

The incorporation of these transmembrane chains into devices can be used to prevent the delamination processes that plague conventional supported bilayer membrane films (FIG. 8). Homologous bolalipids bearing $C_{28}$- and $C_{32}$-transmembrane chains, for example, are compatible with the membrane domain dimensions of P-gp and are synthesized using the reaction pathway described by Thompson and coworkers (Patwardhari et al., *Org. Lett.* 1, 241 (1999)), except that the transmembrane chain contains methyl branching sites and/or olefinic residues to prevent the close packing of alkyl chains that promotes gellation (solidification) of the membrane. A variety of physical techniques, e.g., differential scanning calorimetry, electron spin resonance, and fluorescence recovery after photobleaching, can be used to identify lipids that retain a liquid crystalline state within the 0° C.-37° C. operating temperature range of the device. For further stability, the biofunctionalized membrane can be attached to a extramembranous polymeric scaffold disposed within the aqueous compartment, as described in Example III. Two different approaches, the use of a molecular spring, e.g., a polyethylene glycol (PEG) "mattress," and adsorption onto a porous hydrogel support, can be utilized.

Amphiphilic molecules and dye-modified macromolecules can be used to orient membrane proteins such as P-gp at the surface of the transducer orienting layer and assemble them within durable membrane films. For example, C-terminal histidine-tagged variants of human P-gp can be expressed and purified by metal affinity chromatography. The histidine-tagged proteins interact with $Ni^{2+}$ and ($\alpha$-($\alpha$-lysinenitrilotriacetic acid) (NTA), a property which can be exploited in soft immobilization techniques for protein orientation and immobilization within the membrane films. Orienting molecules, such as bifunctional polyethylene glycols of varying molecular weights that have been modified with $\alpha$-($\alpha$-lysinenitrilotriacetic acid) (NTA) and $\omega$-thiol substituents, can be disposed within or synthesized into the transducer orienting layer. An important factor in the synthesis of nitrilotriacetic acid conjugates is the use of methyl ester protected intermediates until their hydrolysis in the final deprotection step. This approach enables the use of conventional synthetic methodology throughout the pathway and avoids the tedious and difficult separations that would result if free carboxylate intermediates were used instead.

Alternatively, gold electrodes can be used in place of the hydrogel/nanoporous support. The proteins can be immobilized onto the gold electrodes with their drug binding domains oriented away from the electrode surface using bifunctional polyethylene glycols of varying molecular weights that have been modified with $\alpha$-($\alpha$-lysinenitrilotriacetic acid) and co-thiol substituents as described above. Thiol adsorption of these derivatives onto Au orients the NTA ligand toward the aqueous phase where both $Ni^{2+}$ and micellar his-tag P-gp can bind. Addition of bolalipids to these partially coated electrodes, followed by dilution above the critical micellar concentration (CMC), induces self-assembly of planar bolalipid membranes containing highly oriented P-gp. Biotin-streptavidin recognition has been similarly used to produce bacteriorhodopsin supported bilayer films.

Impedance spectroscopy (IS) can be used to detect ion flux across supported bolalipid membrane films. This technology thus advantageously makes use of a new sensor based on either optical or impedance spectroscopic analysis of supported membranes that could greatly accelerate the discovery of new P-gp reversing agents and substrates.

Impedance spectroscopy is capable of providing the sensitivity, simplicity, and speed necessary for reliable analysis. For example, if it is assumed that the reaction chambers are 100 μm×100 μm and 10 nm deep (i.e., the minimum membrane-support separation), the volume of the reaction chamber would be $1 \times 10^{-11}$ $cm^3$. If the starting pH is 7, then there would be $602H^+$ ions within that volume in the absence of other sources of ions. If we further assume that the starting resistivity of the solution within the chamber is 0.1 Ω-cm, then the resistance of such a chamber would be about 1MΩ, which is measurable. The key question, however, concerns the magnitude of the change in resistivity due to a given pH change. For simple electrolytes, this change is approximately linear. Thus, if we have a reaction chamber that initially contains $600H^+$ ions that give a 1MΩ resistance, then the addition of another $60H^+$ ions due to P-gp activity (i.e., a 10% increase) should produce approximately a 100 kΩ change in resistance which is easily measurable. If it assumed that an ATP-driven transducer protein, such as P-gp, is present at a surface density of 1 pump/$\mu m^2$ and that it is capable of releasing 1 $H^+$/sec due to ATP hydrolysis, then a 100 μm×100 μm reaction chamber would have total of $10^4$ pumps, producing a large increase in $H^+$ concentration. It is expected that changes in resistivity arising from P-gp catalyzed ATP hydrolysis will be readily measurable using impedance methods.

Microfluidics. There are currently three techniques for delivering fluids to suitable substrates, e.g. chips, for creating high-density micro-arrays (Schena et al., *TIBTECH* 16, 301-306 (1998)). They are photolithography, contact printing with pin tools, and ink jet printing. These techniques can be contrasted based on their technical as well as cost benefits or drawbacks.

A primary advantage of photolithography, e.g. as developed and practiced by Affymetrix of Santa Clara, Calif., over other techniques is that it is capable of achieving extremely high-density arrays. Theoretically, the technique is capable of creating spot sizes of 10 $\mu^2$, i.e. 10 microns by 10 microns, or smaller. However, the technique is expensive due to the costs associated with creating photomasks.

Contact printing with pin tools, a technique popularized by Patrick Brown of Stanford University, CA, is, by contrast, a relatively inexpensive method for creating arrays. Its drawbacks include the slowness of the arraying process, the requisite contact of the printing tool with the substrate for transfer of the working fluid(s) from the pin to the substrate and the accompanying problem of contamination, and the relative coarseness of the arrays that the method can achieve. This method is unlikely to achieve spot sizes smaller than 100 $\mu^2$ (Rose, *Bio. Techniques Publishing* (2000)).

Inkjet technology allows the production of highly reproducible drops composed of mixtures of one or more components, and ink jet printing is emerging as the most versatile and promising of all arraying techniques. First, it is both a non-contact and a low-cost method of arraying in which the spots are created by ejecting tiny drops from one or (typically) many nozzles onto the substrate. Second, while the current of state-of-the art with ink jet printing is spot sizes of roughly 100 $\mu^2$, the technique is capable of creating arrays approaching the resolution possible with photolithography. Ink jet printing can be carried out in either the continuous (CIJ) or the drop-on-demand (DOD) modes (Le, *J. Imaging Sci Technol*. 42, 49-62 (1998)). Furthermore, the DOD mode can be carried out using either piezo or thermal drop generation methods. To date, virtually all researchers have adopted piezo DOD printing in arraying applications. Regardless of which mode of ink jet printing is used, the method is also extremely fast because a single nozzle of an ink jet arraying system can eject several thousand drops per second.

While ink jet printing has been around for more than 30 years, its scientific underpinnings have only started to be understood recently (Wilkes et al., *Phys. Fluids* 11, 3577-3598 (1999); and Notz et al., *Phys. Fluids* 13, 549-552 (2001)). Drop formation from an ink jet nozzle entails both small length and time scales. Typical nozzle radii R are on the order of tens of microns or less, typical drop sizes $R_d$ are roughly the same as R, and typical drop formation times are on the order of a few or tens of microseconds. Once the drops are formed, they travel through the air and impact the substrate. The drops either successfully deposit on the substrate or else bounce off and/or shatter upon impact. Following successful deposition on the substrate, the drops spread to a final spreading radius or spot size $R_s$ that exceeds $R_d$. The deposition and spreading processes also last on the order of a few or tens of microseconds. Given these scales and the so-called free boundary nature of the drop formation and deposition processes, it is a challenge to describe theoretically and to monitor experimentally the creation of arrays.

Figure 9:
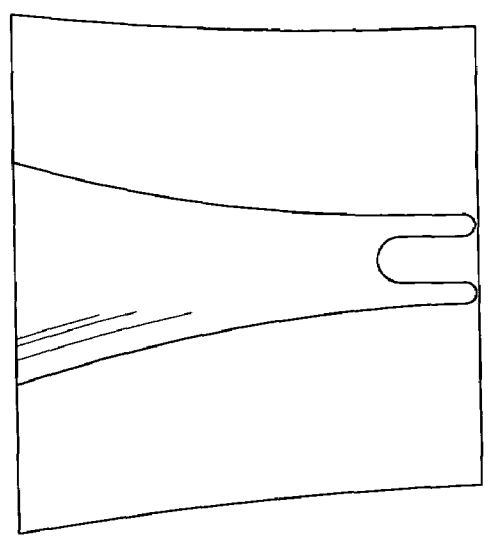
FIG. 9 shows a comparison of drops of 50 wt % glycerol in water produced by using different wave forms.
Figure 9:
Figure 9:
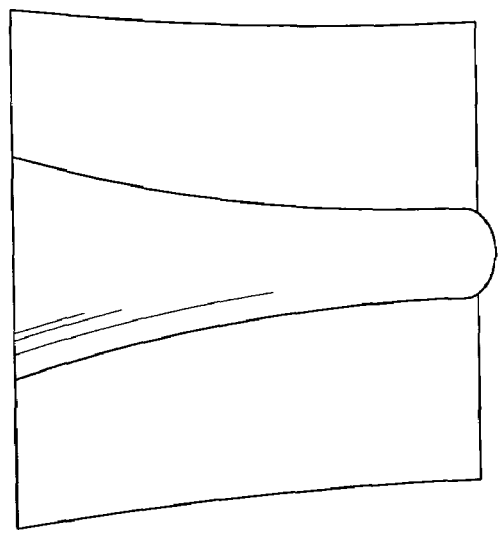
Figure 9:

The objectives of this task are to eject small drops from one or more piezo DOD ink jet nozzles, deposit them on a suitable substrate surface, and ensure the quality of the ejection and deposition processes. Current ink jet drop dispensers are limited in that the radii of drops that they generate are roughly the same as the radii of the nozzles that produce them. We have recently developed a novel method for generating drops with radii much smaller than those of nozzles that produce them (Chen et al., *Phys. Fluids*. (2001)), as shown in FIG. 9. This new method can be implemented to reduce drop size and hence the spot size that can be achieved with ink jet printing. Since the drop liquids may contain lipid particulates and proteins, they are complex non-Newtonian liquids. Thus, successful jetting and deposition of such liquids requires that their surface and bulk rheologies be well characterized (Yildirim et al., *Chem. Eng. Sci*. 56, 211-233 (2001)). Surface characterization tools are used to evaluate solution parameters such as shear and extensional viscosities.

Adsorption of microdrops. Deposition of 10-100 µm diameter microdroplets onto substrate surfaces using ink jet nozzles requires a detailed understanding of the surface properties of both the solid and solution surfaces. The droplets may contain lipid particulates such as multilamellar liposomes, unilamellar vesicles, and micellar solutions of membrane proteins. Since lipid molecules are surface active (adsorb strongly) at both air/water and solid/water interfaces, a portion of them adsorbs onto those surfaces. For the air/water interface, the main consequence is a change in the dynamic surface tension, which affects the drop formation dynamics. For the solid/water interface, the main consequence is the change in the wettability of the solid membrane. For both interfaces, adsorption implies a material loss, which becomes more acute the larger the surface-to-volume ratio and the lower the concentration. Furthermore, protein adsorption on hydrophobic solid surfaces or on water may cause unfolding or denaturation. Hence, interactions of lipids and proteins with interfaces must be controlled, and should be understood at fundamental level.

Adsorption and surface tension of bolalipids and membrane proteins such as P-gp at the air/water and the solid/water interfaces can be evaluated using direct methods such as ellipsometry and at the air/water interface, and similarly at the solid/water interface. The solid/surface can be probed from the liquid side with IRRAS, or from the solid side (where possible) using total internal, reflection IR (or ATR-FTIR). Which component or components adsorb first or ultimately (at equilibrium) can be determined by analyzing dynamically the surface composition. The use of "sacrificial" adsorbates, which may preferentially adsorb and thereby protect the biofunctional bolalipid and P-gp materials, is also envisioned.

Optical sensing techniques and characterization. Read-out of the activity of specific protein-reagent pairs can be achieved using pH sensitive dyes immobilized in the transducer orienting layer. Optical techniques (such as total internal reflection fluorescence (TIRF) microscopy, infrared reflection-adsorption spectroscopy (IRRAS), and ellipsometry) and atomic force microscopy (AFM) techniques can be used to characterize the chemical and physical state of structures containing the biofunctionalized membranes. Immunochemistry techniques can also be used to probe the structure of the films and compare with models of the film at various protein surface loadings. The transport activity of the protein-embedded films (i.e., the biofunctionalized membranes) may be compared with its activity in vesicles (control). Conventional bulk silicon micromachining techniques can be used to fabricate microreactor arrays to which the nanoporous supports are bonded. Inkjet printing, microcontact printing, and/or UV-lithography, for example, can be used assemble the transducer orienting layers and biofunctional asymmetric membranes, and also to introduce the agents to be studied.

Operation of the Device

In operation, the chemical agent to be tested or analyzed (such as a drug, a toxin, or any other naturally occurring or synthetic molecule or molecular complex) is applied to the device via ink jet deposition to the outer or "extracellular" side of the membrane film, and makes its way through the membrane film via diffusion or some other mechanism. Once across the membrane into the aqueous compartment (the "cytosolic" region), the agent potentially induces the activity of the protein transducer such that it is pumped out of the cytosolic region. The activity of the protein transducer can be detected in any number of ways, as illustrated above. In a preferred embodiment, the activity of the protein transducer is detected via the hydrolysis of ATP present in the aqueous compartment.

Operation of one embodiment of the device is illustrated in FIG. 1. The protein transducer, P-gp, is oriented in the membrane film by virtue of the interactions between a $His_6$ tag on the protein and a polyethylene glycol linker in the transducer orienting layer as described in Example III. An analyte is delivered to the outer side of the biofunctional membrane. The analyte moves into and/or across the membrane, binds to P-gp and is pumped out in process driven by ATP hydrolysis. The analyte is effluxed from the outer or ("extracellular") side of the device, and the pump is reactivated.

EXAMPLES

The present invention is illustrated by the following examples. It is to be understood that the particular examples, materials, amounts, and procedures are to be interpreted broadly in accordance with the scope and spirit of the invention as set forth herein.

Example I

Validation of Sensor Performance Using Gramicidin (Ga)

Cyclic voltammetry was used as a probe of supported bolalipid membrane formation on Au electrodes. Immersion of the electrodes into ethanolic solutions of 2 at 25° C. for various times produced surfaces with voltammetric responses that displayed decreasing electrochemical reversibility of $Fe(CN)_6^{3-}$ as 2 deposition increased. (Note that the reference numbers 1 and 2 used in this example refer to bolalipid structures 1 and 2 as shown in FIG. 7.) These data suggest that longer immersion times produced films that were increasingly capable of blocking $Fe(CN)_6^{3-}/Fe(CN)_6^{4-}$ access to the Au surface, such that after 3 hours, the 2 anchor lipid films were deposited as an essentially continuous layer that passivated the surface toward ferri/ferrocyanide redox processes. Time-dependent impedance and phase angle properties of 2-deposited gold electrodes showed similar effects of increasing impedances with increasing deposition time. The experiments described below utilized 60 minutes immersion times for 2 solutions prior to 1 or 1-GA supported membrane depositions.

The effect of GA surface density on supported membrane impedance was determined using electrodes that had been coated with supported bolalipids by pretreatment with 2 prior to immersion for 24 hours into sonicated 1-GA vesicles containing varying amounts of GA. The 1-GA vesicle dispersions were prepared by sonicating dry 1-GA films in water (nominal GA:bolalipid molar ratios ranging from 1:500-1:50; 2 mM total lipid concentration). Impedance measurements with these 1-GAsupported membrane electrodes showed impedance decreases with increasing GA concentration over the entire $1\text{-}10^3$ Hz range, indicating that GA is incorporated within the 1 bolalipid membrane as a functional ion channel. The relatively small changes in impedance observed as the gramicidin:bolalipid ratio was increased by an order of magnitude suggests that ion flux through the channel must be sufficiently fast that increased surface densities of gramicidin channels has little influence on impedance behavior. This observation is consistent with $^{23}Na$ NMR ion flux measurements made previously in our laboratory for gramicidin-containing 1 vesicles.

Figure 10:
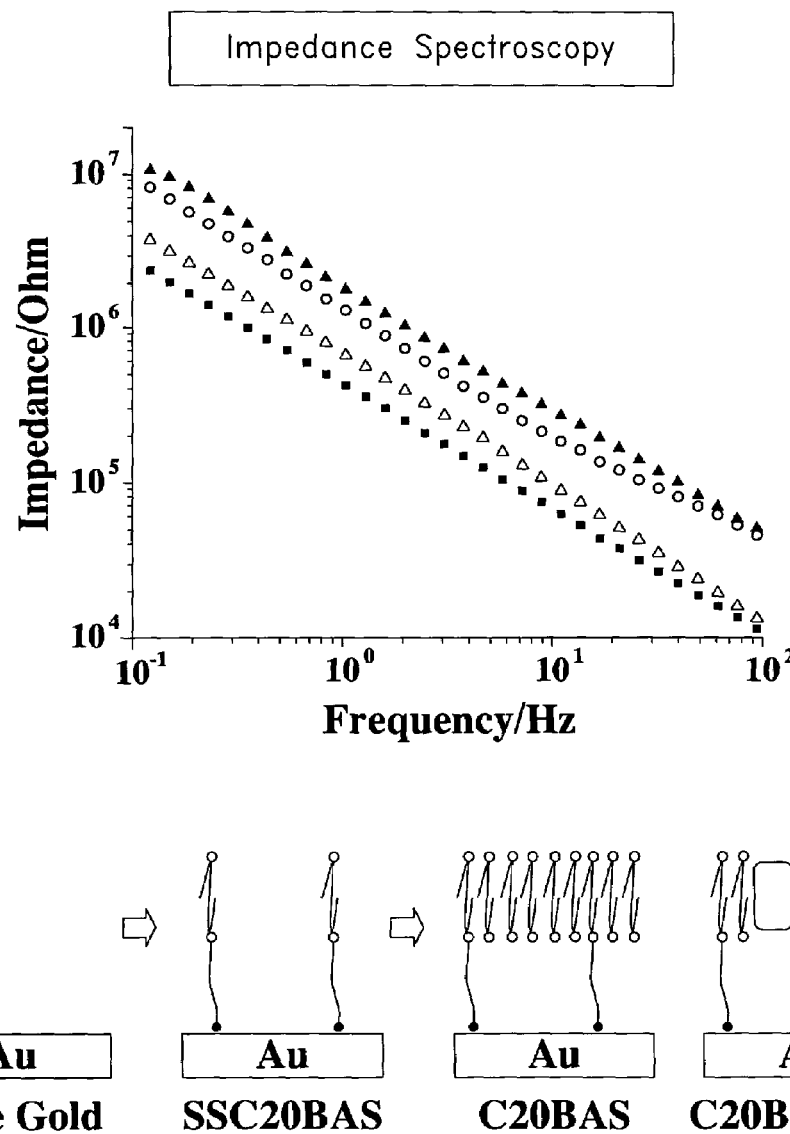
FIG. 10 shows impedance behavior of Au electrodes during sequential deposition onto Au electrodes: bare Au electrodes; addition of SSC20BAS (2); addition of C20BAS (2+1); and addition of gramicidin (2+1+gramicidin), wherein reference numbers 1 and 2 refer to the lipids in FIG. 7.
Figure 11:
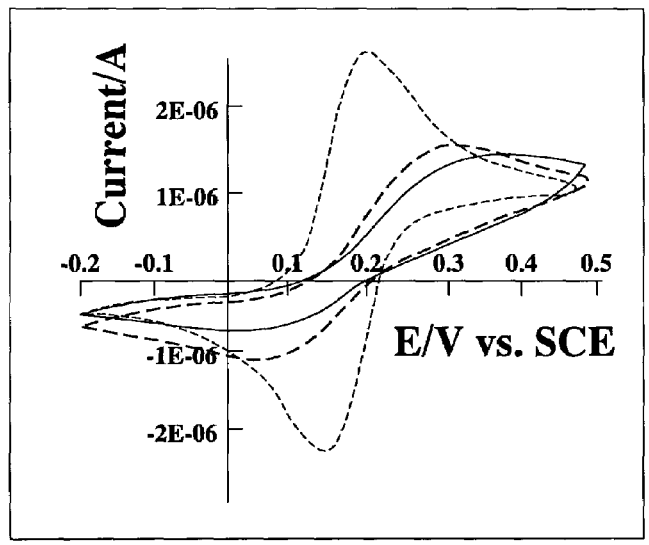
FIG. 11 shows solvent resistance of supported membranes on Au electrodes (A) SSC20BAS-DPPC; (B) SSC20BAS-C20BAS-GA.
Figure 11:
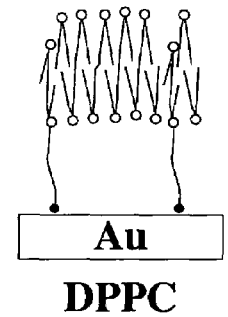
Figure 11:
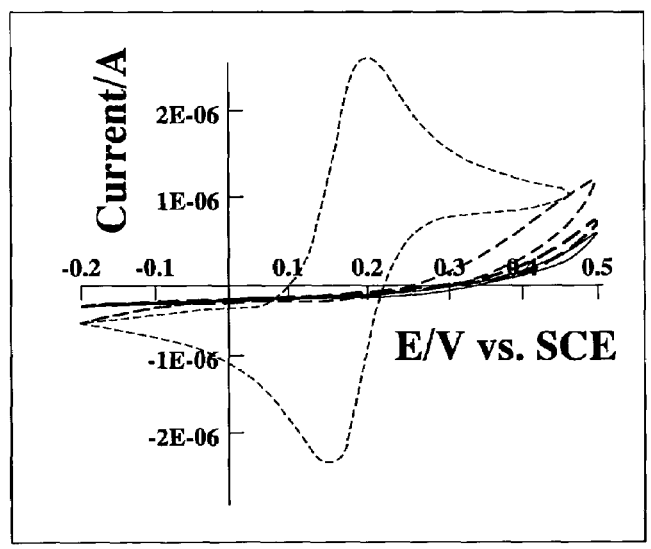
Figure 11:
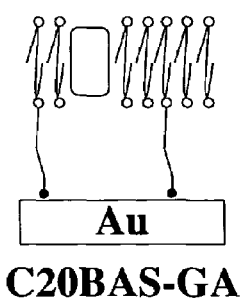

The effects of gramicidin loading on supported bolalipid membrane electrode impedance was further investigated in a sequential deposition experiment (FIG. 10). Adsorption of 2 onto Au electrodes for 1 hour to give partial surface coverage produced significant increases in impedance. Immersion of these pretreated electrodes into bolalipid vesicle solutions where gramicidin was either absent or present (i.e. 1 and 1-GA vesicles, respectively) produced membrane coated electrodes that had substantially different impedance characteristics in $10^{-1}\text{-}10^2$ Hz frequency range. As the data in FIG. 11 show, immersion of the 2-treated electrode into 2 mM 1 membrane solutions for 24 hours further increased the sensor impedance, due to vesicle-surface fusion with formation of a continuous, impermeable 1 membrane with high-impedance. When the 2 electrodes were immersed in 1-GA membrane solutions for 24 hours (1:100 molar ratio GA:1), however, the observed impedances were lower—approaching that of bare Au—than for either the 2 or 2-1 supported bolalipid membrane coatings. These data further support the involvement of GA as an ion transporter in these supported membrane constructs. We also infer from these results that the 1 hour pretreatment of gold with ethanolic solutions of 2 produces films that are disordered and discontinuous (i.e. containing defect sites due to low surface coverages and/or poor bolalipid packing). These disordered surfaces become well-ordered upon adsorption and fusion of bolalipid vesicle dispersions onto the partially-covered electrode surfaces. When 1 vesicles are used (i.e. gramicidin-free bolalipid vesicles), higher impedances are observed due to the annealing of surface defects by the more highly ordered 1 membrane. When 1-GA vesicles are used, the highly ordered 1 monolayer membranes nonetheless produce Au electrode surfaces with lower impedance due to the activity of monomeric GA channels that are actively transporting cations across the supported membrane films.

Figure 12:
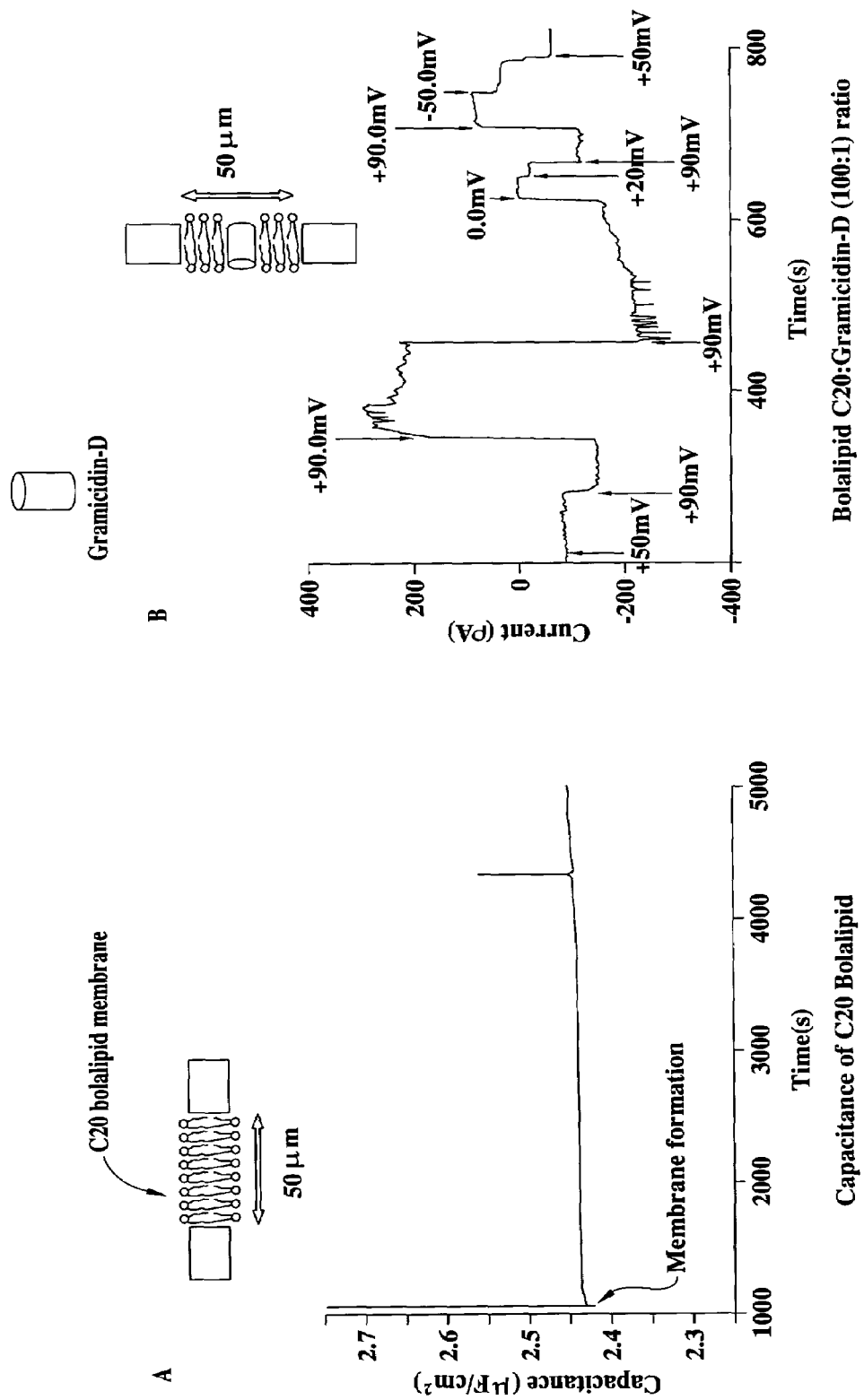
FIG. 12 shows capacitance and single channel measurements (A) capacitance of C20 bolalipid; (B) bolalipid C20: gramacidin-D (100:1 ratio).

Capacitance experiments (FIG. 12) also showed that C20 bolalipid membranes, without gramicidin, exhibited no ion flux, whereas addition of gramicidin to the monolayer resulted in ion flux across the membrane.

Gold electrodes bearing supported bolalipid membranes are also remarkably rugged compared to conventional supported bilayer membranes. Cyclic voltammetry experiments reveal that sequential washings with water, ethanol, and methylene chloride had relatively little effect on the voltammetric response of membrane-treated Au electrodes (FIG. 11). This contrasts with the behavior of DPPC-based supported membrane electrodes prepared in a similar manner, which displayed far less resilience toward identical solvent treatments that the bolalipid membrane surfaces. These films are presumably more robust because the membranes are more highly-ordered than the DPPC films where hydrophobic mismatch between the bilayer and SSC20BAS monolayer lipids creates solvent-accessible defect sites.

Example II

Hydrogel Layer/Support Structure

Monomers or polymers are loaded into the micropores of the solid support material using ink-jet methods. The hydrogel support inside the micropores can be prepared by two methods: crosslinking polymerization of monomers and crosslinking reactions of water-soluble polymers. Since it is desirable to have the chemically active functional moieties on the polymer backbone, chemically active monomers or polymers are preferred The following monomers and polymers are good candidates for making hydrogels.

1. Monomers that can react with the hydroxyl groups of proteins or polysaccharides (e.g. acryloyl chloride and glycidyl acrylate)
2. Monomers that can react with amine groups of proteins and polysaccharides (e.g. methacryloyl chloride, acryloxyethylisocyanate, allyl glycidyl ether, and acrolein)
3. Monomers that can react with carboxyl groups of proteins or polysaccharides (e.g. vinyl acetate)

The above monomers are used in conjunction with other monomers that are chemically inert. They are acrylamide, vinylpyrrolidone, and hydroxyethyl methacrylate, for example. The chemically active groups of the functional monomers are used to covalently graft P-gp proteins to the hydrogel surface. Once P-gp is grafted to the hydrogel surface, the remaining functional groups are quenched by using suitable small molecular weight quenchers, such as amino acids.

Polymers to form hydrogels. Water-soluble polymers that can react with bifunctional crosslinking agents can be used to form chemical gels. Examples include:

1. Polymers containing hydroxyl groups (e.g. dextran, starch)
   These polymers can be crosslinked with bis(epoxy propyl) ether, divinyl sulfone, carbonyldiimidazole, epichlorohydrin, and glutaraldehyde.
2. Polymers containing amine groups.
   These polymers can be crosslinked with bisimidate, bis(sulfonsuccinimidyl) suberate, bis(p-nitrophenyl) adipate, bisepoxide, and glutaraldehyde.
3. Polymers containing carboxyl groups.
   Polyepoxides have been used frequently to crosslink this type of polymer. Water-soluble polymers can also be made into physical gels using non-covalent crosslinks. Physical gels can be formed by ionic associations, hydrophobic interactions, and stereocomplex formation, for example. The most commonly used method in biomedical and pharmaceutical areas is the calcium ion-induced gelation of sodium alginate.

Any monomer and/or polymer described above can be used for:

1. Crosslinking polymerization. Monomers (e.g., acryloyl chloride, glycidyl acrylate, or acrolein) are mixed with acrylamide or vinylpyrrolidone with the molar concentration of chemically active monomers ranging from 1 mol % to 30 mol %. A crosslinking agent, such as bisacrylamide, is added and its concentration is varied from 1 mol % to 10 mol % of monomers. Azobisisobutyronitrile is used as the initiator at the concentration of 1 mol % of monomers. Once the hydrogel is formed, the chemically active groups are used for covalent grafting of proteins to the surface of the formed hydrogels. Once the grafting is complete, the remaining functional groups are deactivated by adding excess glycine.

2. Physical gelation. Sodium alginate is mixed with ATP before introduction into the micropores. The concentration of sodium alginate will be maintained at about 1 w/v %. From our experience, the viscosity of alginate in this concentration range is high enough for using ink jet dispensers. At the same time, the concentration is also high enough to form physical gels in the presence of calcium ions. Once sodium alginate is filled in the pores, the bottom layer of the solid support will be immersed into a calcium ion solution so that the gelation begins from the surface. Once the gel is formed, the carboxyl groups of alginate molecules are used for chemical grafting of proteins to the hydrogel surface. If the increase in the thickness of the hydrogel layer is necessary, the alginate gel can be exposed to poly(L-lysine) solution (0.1 w/v %) to coat the hydrogel surface with polycation. Then, the amine groups of the poly(L-lysine) can be used for further chemical modification, or additional alginate can be immobilized on top of the polycations. This process can be repeated as needed to increase the device durability.

One of the advantages physical gelation over crosslinking polymerization is that the gelation process is very simple and, at the same time, easy to control the regions between the polymer chains that influence the diffusion rate of molecules inside the hydrogel. The concentrations of sodium alginate and calcium ions, as well as the time of calcium ion diffusion into the alginate gel, can be adjusted to obtain physical gels of the desirable properties.

Example III

P-glycoprotein Isolation and Formation of the Biofunctionalized Membrane

P-gp can be tagged with 6-10 histidine residues at the C-terminus without affecting function. Wild-type P-gp containing a six histidine tag at the C-terminus (P-gp-$H_6$) was purified from insect cells using metal affinity chromatography. P-gp-$H_6$ has been shown to be 85% pure as indicated by silver staining. Using the rapid dilution method to reconstitute the protein into proteoliposomes, Vi-sensitive drug stimulated ATPase activity of P-gp-$H_6$ was determined. The reconstituted protein demonstrated high specific activity (5.8 µmol/min/mg protein) in the presence of 30 µM verapamil. This rapid dilution method reconstitutes approximately 20% of the starting material, 50% of which is catalytically active, as determined by permeabilization of proteoliposomal membranes with alamethicin. Therefore, after reconstitution, only 10% of the input protein is accessible for the measurement of ATPase activity. This yield of functional P-gp was used to calculate the specific activity of the protein.

Vanadate ($V_i$)-sensitive ATPase activity can be measured in proteoliposomes reconstituted with purified P-gp-H using the following assay. Purified protein (0.35-0.45 µg/mL) containing 1.25% octylglucoside and 0.1% lipid mixture is rapidly diluted 20-fold to reconstitute P-gp into proteoliposomes in a 13×100 mm glass test tube in a reaction mixture containing 50 mM Tris-HCl (pH 6.8), 125 mM KCl, 5 mM $MgCl_2$, and 1 mM dithiothreitol (DTT) in the presence or absence of 300 µM sodium orthovanadate and incubated at 37° C. for 3 minutes. Subsequently, 1 µL of dimethyl sulfoxide (DMSO) or 3 mM verapamil (prepared in DMSO) is added and the reaction mixture incubated for an additional 3 min at 37° C. The reactions are started by the addition of 2.5 mM ATP and incubated at 37° C. for 20 minutes. The reactions are stopped by the addition of an equal volume of 5% (v:v) sodium dodecyl sulfate (SDS) and the amount of phosphate released determined spectrophotometrically.

The protein is immobilized onto a nanoporous/hydrogel membrane support with the drug binding domains oriented away from the support. This can be accomplished using bifunctional polyethylene glycols (Sackmann, *Science* 271, 43 (1996); and Wong et al., *Biophys. J.* 77, 1445 (1999)) of varying MW's that have been modified with α-(α-lysinenitrilotriacetic acid) (NTA) and co-thiol substituents. Reaction of the thiol substituent with the underlying support layer orients the NTA ligand toward the aqueous phase where both $Ni^{2+}$ and micellar his-tag P-gp can bind.

When electrochemical detection methods are preferred in the specific application, his-tagged membrane proteins are added to gold electrodes that are partially coated with the same bifunctional polyethylene glycols bearing α-(α-lysinenitrilotriacetic acid) (NTA) and ω-thiol substituents as described above. Dilution of the oriented membrane proteins below the CMC of the protein-solubilizing detergent by addition of a large excess of bolalipid vesicles is expected to induce self-assembly of planar bolalipid membrane films containing highly oriented P-gp. Biotin-streptavidin recognition has been similarly used to produce bacteriorhodopsin supported bilayer films (Bieri et al., *Nature Biotechnology* 17, 1105-1108 (1999)). The resulting biofunctionalized membranes are now configured to detect membrane protein-mediated events via their effect on impedance at the gold electrode surface.

Monoclonal antibodies directed against the histidine tag can be used as confirmation of orientation. The orientation of P-gp in these supported membrane structures can be further established by differential recognition of the protein with antibodies specific for distinct sites on the protein. Three monoclonal antibodies that recognize human P-glycoprotein have been developed. MRK-16 is specific for an external epitope in the first extracellular loop of human P-gp whereas C219 (Kartner et al., *Nature* 316, 820 (1985)) recognizes regions within the internal cytoplasmic nucleotide binding domains. UIC2, a conformationally-sensitive antibody whose reactivity is increased in the presence of P-gp transport substrates, ATP-depleting agents, or mutations that reduce the level of nucleotide binding by P-gp, is also specific for the external portion of the protein. Use of these antibodies is expected to allow for the recognition of either side of P-gp after reconstitution of the protein into the supported membrane environment and aid in determining the functional state of the protein.

Alternatively, other epitope tags—including myc and FLAG tags—can be genetically engineered into the C-terminus and the first extracellular loop of P-gp. Insertions and limited deletions of these regions have been shown to have little to no effect on P-gp function. The addition of these epitope tags to the N-terminus and the effect of the insertion on function is evaluated. Orientation of these proteins in the supported membrane can be assessed by antibody recognition using commercially available antibodies.

If P-gp activity is compromised because the trapped water compartment is small and prevents coupling of the two ATP binding sites, different MW PEGs can be used as flexible spacers. If these undergo delamination, the mechanical rigidity of the support can be increased using dextran films.

If P-gp activity is affected by membrane viscosity and/or specific lipid components within the biofunctionalized membrane, bolalipids containing an increasing density of methyl branching sites at the membrane core can be used. These bolalipids represent a family of membrane materials whose phase transition temperatures (Tm) are near 15° C. The biofunctionalized membrane formed from these materials produces gel phase films at 25° C. where most experiments will be performed. If low p-gp activity is still observed, activity at higher temperatures (i.e. reduced microviscosity) or in the presence of mixed bolalipid-conventional lipid films (i.e. specific lipid requirement) can be evaluated.

Example IV

Connection of the Biofunctionalized Membrane to the Hydrogel Matrix

Hydrophilic polymers can be employed within the aqueous compartment housing the membrane film to connect the hydrogel support matrix to the membrane film to provide greater mechanical strength. The molecular entities used to chemically or physically connect the biofunctionalized membrane to the hydrogel matrix are selected so as to optimize the separation distance between the two structures. This is important since the ABC site of P-gp may protrude 50 Å or more beyond the membrane film interface toward the nanoporous substrate surface. If this distance is not carefully controlled, the activity of P-gp (within an otherwise intact structure) may be lost. Hydrophilic polymers are selected that optimize polymer molecular weight, surface density and chemical or physical attachment to achieve the best stabilized supported membrane.

A molecular based theoretical methodology that enables the calculation of the structural and thermodynamic properties of tethered polymer layers (Szleifer et al., *Adv. Chem. Phys.* Vol. XCIV, Chap. 3, pgs. 165-260 (1996); Szleifer, *Science* 2, 337-344 (1997); and Szleifer et al., *Macromolecular Rapid Communications* 21, 423448 (2000)) can be used to aid in the selection process. The predictions of the theory have been shown to be in excellent quantitative agreement with experimental observations of pressure-area isotherms of PEG tethered chains (Faure et al., *Eur. Phys. J.B* 3, 365-375 (1998)), the ability of PEG to reduce protein adsorption on hydrophobic surfaces (McPherson et al., *Langmuir* 14, 176-186 (1998); and Satulovsky et al., *Proc. Nat. Acad. Sci.* 97, 9037-9041 (2000)) and the effect of PEG to stabilize liposomes (Szleifer et al., *Proc. Nat. Acad. Sci.* 95, 1032-1037 (1998)).

To showcase the different possible supports that one can design, and the possible consequences of not having the proper polymer layer, theoretical calculations were performed on two different scenarios. In the first, the interaction between two surfaces wherein the polymers are chemically attached to both surfaces was examined. The model polymers corresponded to PEG-2200, and two surface coverages were examined. In both cases, the interactions between the surfaces had pronounced minima that slightly moved toward larger distances when the surface density of polymer was increased. Further, the curvature of the interaction was much larger for larger surface coverage, implying that the membrane will have smaller fluctuations at larger surface coverages.

The second case corresponds to PEG-1000 that is chemically bound to the matrix, but interacts with the lipid bilayer that forms the membrane film through a charged functionalized end-group in the PEG chain. The results correspond to relatively high surface coverages of polymer and low salt concentration.

The shape of the potential in the second case was very different than for the first case. First, the attractive interaction showed a constant value over a relatively large range of distances. Second, the repulsions at short distance were very sharp relative to the other case. This interaction may cause the biofunctionalized membrane to become highly delocalized throughout the minimal interaction region. Further, this potential is very sensitive to salt concentration, suggesting that it may change as P-gp transport of molecules occurs, if care is not taken to keep the concentration of charged species constant.

These two examples show that the proper choice of surface coverage, molecular weight and type of attachment (chemical or physical) of the polymer to the surface is important for the proper design of the biofunctionalized membrane. A further complication that needs to be avoided is that the concentration of polymer in the supporting region be small enough so that the analytes can reach and interact with the sensing molecules.

Tethering of the hydrophilic polymers such as PEG to the support structure and the biofunctionalized membrane can be accomplished by, for example, covalent bonds at both ends of the hydrophilic polymer, or by a combination of covalent linkages and electrostatic interactions.

Double covalently-tethered chains. This corresponds to the case in which the PEG molecules are chemically bonded to both the lipid and matrix. The optimal distance between the aggregate and the hydrogel matrix is expected to be on the order of 100 Å. Polymer molecular weight and range of surface coverage is selected for which the minimum in the surface-surface interaction term is within 5 Å from the optimal distance. The choice of surface coverage is preferably the minimal amount necessary to have interaction strength around the optimal distance yet still enable the necessary freedom of membrane fluctuation.

Covalent and electrostatically-tethered chains. This corresponds to the case of a chemical link between the polymer and the hydrogel matrix, and an electrostatic interaction—through the functionalized free-end of the polymer—with charged lipids in the membrane. This may be a preferred configuration if covalent binding of the polymers to both interfaces results in very restricted lateral motion of the lipids and protein on the membrane. The stability of the electrostatic interactions needs to be examined with respect to changes in salt concentration that may arise from the transport of drug candidates through the membrane.

Example V

Microfabrication

The reaction chambers are fabricated using standard bulk micromachining techniques. Specifically, (100) silicon wafers with a boron etch stop embedded under 10 μm of silicon are acquired from a commercial source. The wafer is patterned using standard spin coating, exposure, and development protocols, and an anisotropic through etch will be used to form the reaction chambers. The optimum thickness of the silicon and etch stop conditions are determined. The silicon reaction chamber is bonded to commercially available nanoporous membranes that are approximately 100 μm thick. After the bonding has been established the wafer supporting the reaction chambers are removed by back etching. Anodic etching protocols that produce nanoporous membranes that are bout 10 μm thick are utilized.

Example VI

Characterization of the Biofunctionalized Membrane

Signal Detection Techniques. Drug transport by P-gp requires ATP hydrolysis. Our sensor architecture utilizes ATP hydrolysis as the basis for signal generation. This design generates a predictable response as a result of drug-stimulated ATPase activity at 0.3-1.4 mM ATP levels. Impedance spectroscopy (IS) is well-suited for monitoring millimolar level changes in ionic conductance, therefore, this detection scheme is preferred over those based on efflux of drugs whose physicochemical properties differ widely. Initially, IS of unbuffered ATP solutions in the trapped aqueous layer is used to establish detection limits as a function of P-gp loading density on the electrode surface.

If high background signal levels are observed due to basal, unstimulated ATPase activity that may occur prior to chemosensitizer activation, background can be suppressed by using materials with solid-gel melting transitions in the 10-15° C. range. Solidification of these films at 5° C. restricts the P-gp conformational freedom required for pumping and ATPase activity. Heating above Tm before IS analysis restores ATPase capacity. If ADP inhibition of ATPase activity limits the sensitivity achievable via IS technique, amperometric or pH detection can be adopted as an alternative.

Atomic Force Microscopy. During the past decade, the atomic force microscope (AFM) has become a key technique for the characterization of supported lipid films. The unique capabilities of the AFM include: (i) ability to probe, in real time and in aqueous environment, the surface structure of lipid films; (ii) ability to directly measure physical properties (i.e., thickness, surface forces, and elastic modulus) with nanometer scale spatial resolution. AFM can be used to characterize the lipid films at the solid liquid interface (Dufrene et al., *Biomembranes* 1509, 14-41 (2000); Schneider et al., *Biophysical Journal* 79, 1107-1118 (2000); and Dufrene et al., *Faraday Discussions* 111, 79-94 (1999)) to guide the work on forming orientating P-gp layers and designing novel membranes to support these proteins. Specifically, the high spatial imaging capabilities of the microscope can be used to visualize the distribution of P-gp at the solid liquid interface and characterize the quality of the lipid bilayer formed around the protein. Surface forces and mechanical measurements can be used to characterize mechanisms of adsorption and stability of the film.

Ellipsometry, IRRAS and Total Internal Reflection Microscopy. Films can be characterized with ellipsometry, which probes films by measuring the reflectance and change of phase of polarized light beams. For better sensitivity, multiple incident angles and wavelengths will be used (Walsh et al., *J. Colloid Interf. Sci.* 233, 295-305 (2001); and Walsh et al., *Thin Solid Films* 347, 167-177 (1999)). The measured ellipsometric parameters (angles $\Delta$ and $\psi$) can be used in solving inverse problems for determining thickness d, refractive index, and anisotropy of transparent or absorbing films for 0.01 μm to about 1 μm. For thinner films, only a combination of thickness and refractive index can be determined, or the surface density of surfactants or lipid membranes.

In addition, infrared spectroscopy can be used to characterize surface densities of particular molecules, and their average orientation and chain conformation. Primarily, the IRRAS (reflection absorption) spectroscopy will be used, for layers as thin as 1-2 nm and as thick as 0.1 μm.

Total internal reflection (TIR) fluorescence microscopy combines the standard features of an epifluorescence microscope with unique evanescent wave excitation optics. At the interface between a quartz prism through which a laser beam comes in at a large incidence angle and totally reflected, and a thin sample layer over which the electromagnetic field does not abruptly drop to zero but decays exponentially. This surface electromagnetic field, called the "evanescent wave," can selectively excite fluorescent molecules in the thin liquid layer within 100 nm of the interface. The unique advantage of this design of optical path over others is that the background noise due to the illuminating beam is completely rejected by total internal reflection (TIR). The technique has been shown ideally suited for detecting single fluorescent molecules such as a molecular motor moving along some fixed track or a labeled ligand attached to a large functional complex. The TIR microscopy is well suited for characterizing asymmetric membrane as the transfer of labeled protein across the lipid bi-layer is expected to cause a detectable change of signal. The technique is also well suited for detecting slow migration of a labeled protein probe within a 2-dimensional membrane fluid.

A second optical technique that is useful for structural characterization of asymmetric membranes is by measurement of local birefringence. Lipid membranes are know to be liquid crystalline materials, which interact with polarized light in ways that can be measured using a special polarization optics setup (Oldenbourg et al., *J. of Microscopy* 180, 140-147 (1995)). The sensitivity of the existing setup is better than a nanometer of the retardance value, with spatial resolution of a few micrometers using a 40× objective. It is useful for detecting changes within individual micro-arrays of the composite membrane, such as the layer thickness and the local molecular orientation.

A third technique is a setup for microelectronic measurements. Our approach is similar to that developed to count polymers moving through a single ion channel (Bezrukov et al., *Nature* 370, 279-281 (1994)), except that the membrane will be laid flat on a homemade holder, with two electrodes above and below the membrane surface submerged in the aqueous medium. The measured electric conductivity signal through the composite membrane provides an independent report of membrane permeability to small ions of interest. In addition, since the whole device can be placed on a microscope stage, the conductivity measurements can be combined with optical microscopy, including direct visualization of protein probes in the same membrane array using fluorescent tags.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A bioanalytical device comprising:
   (a) a membrane film including monolayer membrane components selected from the group consisting of bolalipids, bolaamphiphiles, and amphiphilic tri-block copolymers, said membrane having an outer surface and an inner surface;
   (b) a support substrate in fluid communication with the inner surface of the membrane film and defining an aqueous compartment between the membrane film and the support substrate;
   (c) a transducer orienting layer overlapping said substrate and including orienting moieties effective for orienting a protein transducer; and
   (d) a protein transducer within said membrane film and directionally oriented therewith by interaction with said orienting moieties of said transducer orienting layer.

2. (The bioanalytical device of claim 1, wherein said interaction of said protein transducer and said transducer orienting layer is reversible.

3. The bioanalytical device of claim 1, wherein said interaction of said protein transducer and said transducer orienting layer is irreversible.

4. The bioanalytical device of claim 1, wherein a single layer functions as said support substrate and said transducer orienting layer.

5. The bioanalytical device of claim 1, wherein said transducer orienting layer includes polyethylene glycol.

6. The bioanalytical device of claim 5, wherein said orienting moieties include α-(α-lysinenitrilotriacetic acid (NTA).

7. The bioanalytical device of claim 1, wherein said membrane component includes a bolalipid.

8. The bioanalytical device of claim 1, wherein said membrane component includes a bolaamphiphile.

9. The bioanalytical device of claim 1, wherein said membrane component includes an amphiphilic tri-block copolymer.

10. The bioanalytical device of claim 1, wherein said orienting moieties include affinity tags selected from the group consisting of His-, Myc-, FLAG-, and HA-.

11. The bioanalytical device of claim 10, wherein said affinity tag is a polyhistidine-$Ni^{2+}$-NTA moiety.

12. The bioanalytical device of claim 1 wherein the transducer orienting layer comprises a detection moiety for detecting the activity of the protein transducer.

13. The bioanalytical device of claim 1 wherein said protein transducer is in a perpetual "on" state allowing an analyte constant passage through said membrane film.

14. A method for analyzing an analyte comprising: contacting the analyte with the outer surface of the membrane film of a device as in claim 1, such that the analyte passes into or across the membrane film; and detecting the activity of the protein transducer, wherein activity of the protein transducer is indicative of the efflux of the analyte from the outer surface of the membrane film.

15. The method of claim 14, wherein the analyte is a candidate drug.

16. A bioanalytical device comprising:
   (a) a monolayer membrane film having an outer surface and an inner surface;
   (b) a support substrate in fluid communication with the inner surface of the membrane film and defining an aqueous compartment between the membrane film and the support substrate.
   (c) a transducer orienting layer overlapping said substrate and including orienting moieties effective for orienting a protein transducer; and
   (d) a protein transducer within said membrane film, wherein said transducer is directionally oriented therewith by interaction with said orienting moieties of said transducer orienting layer and in a perpetual "on" state allowing an analyte constant passage through said membrane film.

17. The bioanalytical device of claim 16, wherein said membrane film includes a component selected from the group consisting of bolalipids, bolaamphiphiles, and amphiphilic tri-block copolymers.

18. The bioanalytical device of claim 16 wherein the bioanalytical device is fabricated as a replaceable cartridge.

19. A method for identifying an inhibitor of a protein transducer comprising: contacting the outer surface of the membrane film of a device as in claim 16 with:
   (a) an analyte capable of being actively transported by the protein transducer, wherein the protein transducer is a membrane-embedded protein transducer and (b) a candidate inhibitor of the protein transducer; and determining whether the active transport of the analyte by the membrane-embedded protein transducer is inhibited by the candidate compared to the active transport of the analyte by the membrane-embedded protein transducer in the absence of the candidate inhibitor.

20. A method for making a bioanalytical device comprising:
   (a) applying a hydrogel precursor solution to the surface of a support substrate;
   (b) applying a gellating agent to the hydrogel precursor to cause gellation of the hydrogel precursors to yield a transducer orienting layer in physical contact with the surface of the support substrate, said transducer orienting layer including terminal orienting moieties for orienting a protein transducer;
   (c) applying a protein transducer and a membrane film material to said transducer orienting layer to yield a membrane film having said protein transducer oriented with said membrane film through said orienting moieties and an inner surface defining an aqueous compartment providing communication between said membrane film and said transducer orienting layer, said film material including at least one component selected from the group consisting of bolalipids, bolaamphiphiles, and amphiphilic tri-block copolymers.

21. The method of claim 20, wherein the transducer orienting layer is integrated into the support substrate.

* * * * *